(12) United States Patent
Taylor

(10) Patent No.: US 12,286,629 B2
(45) Date of Patent: Apr. 29, 2025

(54) COMPOSITIONS AND METHODS FOR TREATING ENDOMETRIOSIS

(71) Applicant: YALE UNIVERSITY, New Haven, CT (US)

(72) Inventor: Hugh Taylor, Easton, CT (US)

(73) Assignee: YALE UNIVERSITY

( * ) Notice: Subject to any disclaimer, the term of this patent is extended or adjusted under 35 U.S.C. 154(b) by 125 days.

(21) Appl. No.: 17/258,879

(22) PCT Filed: Jul. 12, 2019

(86) PCT No.: PCT/US2019/041532
§ 371 (c)(1),
(2) Date: Jan. 8, 2021

(87) PCT Pub. No.: WO2020/014566
PCT Pub. Date: Jan. 16, 2020

(65) Prior Publication Data
US 2021/0324385 A1    Oct. 21, 2021

Related U.S. Application Data

(60) Provisional application No. 62/697,457, filed on Jul. 13, 2018.

(51) Int. Cl.
*C12N 15/113* (2010.01)
*A61P 15/00* (2006.01)

(52) U.S. Cl.
CPC .......... *C12N 15/1137* (2013.01); *A61P 15/00* (2018.01); *C12N 2310/141* (2013.01); *C12N 2310/531* (2013.01)

(58) Field of Classification Search
CPC .......... C12N 15/1137; C12N 2310/141; C12N 2310/531; A61P 15/00
See application file for complete search history.

(56) References Cited

U.S. PATENT DOCUMENTS

| | | | |
|---|---|---|---|
| 10,982,282 B2 | 4/2021 | Taylor | |
| 11,220,713 B2 | 1/2022 | Taylor | |
| 2008/0141715 A1* | 6/2008 | Chakravarthy | A61L 2/022 62/65 |
| 2009/0220589 A1* | 9/2009 | Trieu | A61P 35/00 435/6.12 |
| 2009/0317820 A1 | 12/2009 | Wong | |
| 2012/0172416 A1 | 7/2012 | Velin | |
| 2014/0024590 A1 | 1/2014 | Weidhaas | |
| 2014/0342937 A1 | 11/2014 | Jeanson-Leh | |
| 2014/0377263 A1* | 12/2014 | Lieberman | A61P 35/00 424/174.1 |
| 2015/0267257 A1 | 9/2015 | Nagarkatti | |
| 2017/0029822 A1* | 2/2017 | Saragovi | A61P 27/16 |
| 2017/0175190 A1 | 6/2017 | Taylor | |
| 2019/0276893 A1 | 9/2019 | Taylor | |
| 2020/0206303 A1 | 7/2020 | Bowerman | |
| 2020/0321077 A1 | 10/2020 | Taylor | |
| 2022/0049312 A1 | 2/2022 | Taylor | |

FOREIGN PATENT DOCUMENTS

| | | | |
|---|---|---|---|
| CN | 103237901 | 8/2013 | |
| EP | 2924126 | 9/2015 | |
| JP | 2014513521 A | 6/2014 | |
| JP | 2015504655 A | 2/2015 | |
| WO | 2010056337 A2 | 5/2010 | |
| WO | 2012103355 A2 | 8/2012 | |
| WO | 2012112883 | 8/2012 | |
| WO | WO-2013109604 A1 * | 7/2013 | ........... A61K 39/245 |
| WO | 2013148151 A1 | 10/2013 | |
| WO | 2015073972 A1 | 5/2015 | |
| WO | 2015128671 A1 | 9/2015 | |
| WO | 2015148919 | 10/2015 | |
| WO | 2018044979 A1 | 3/2018 | |
| WO | 2019046494 | 3/2019 | |
| WO | 2020092672 | 5/2020 | |
| WO | 2020223238 | 11/2020 | |

OTHER PUBLICATIONS

Seifer BJ, Su D, Taylor HS. Circulating miRNAs in Murine Experimental Endometriosis: Decreased Abundance of let-7a. Reproductive Sciences. 2017;24(3):376-381.
Shibahara, Yukiko et al. "Aromatase inhibitor treatment of breast cancer cells increases the expression of let-7f, a microRNA targeting CYP19A1." The Journal of pathology vol. 227,3 (2012): 357-66. doi: 10.1002/path.4019.
Simoens, S et al. "Endometriosis: cost estimates and methodological perspective." Human reproduction update vol. 13,4 (2007): 395-404. doi:10.1093/humupd/dmm010.
Small, Eric M., and Eric N. Olson. "Pervasive roles of microRNAs in cardiovascular biology." Nature 469.7330 (2011): 336-342.
Sredni et al., 2011, "A Parallel Study of mRNA and microRNA Profiling of Peripheral Blood in Young Adult Women." Front Genet, 2:49 (6 pages).
Suryawanshi et al., 2013, "Plasma microRNAs as novel biomarkers for endometriosis and endometriosis-associated ovarian cancer." Clin Cancer Res, 19:1213-1224.
Takamizawa, Junichi et al. "Reduced expression of the let-7 microRNAs in human lung cancers in association with shortened postoperative survival." Cancer research vol. 64,11 (2004): 3753-6. doi:10.1158/0008-5472.CAN-04-0637.
Takebayashi, Akie et al. "Subpopulations of macrophages within eutopic endometrium of endometriosis patients." American journal of reproductive immunology (New York, N.Y. : 1989) vol. 73,3 (2015): 221-31. doi:10.1111/aji. 12331.
Taylor, et al. Treatment of Endometriosis-Associated Pain with Elagolix, an Oral GnRH Antagonist.. N Engl J Med. Jul. 6, 2017;377(1):28-40.

(Continued)

*Primary Examiner* — J. E. Angell
(74) *Attorney, Agent, or Firm* — Riverside Law LLP

(57) ABSTRACT

The invention includes compositions and methods for the treating or preventing endometriosis in a subject in need thereof. In one aspect, the invention relates to compositions and methods for modulating let-7 microRNA.

1 Claim, 7 Drawing Sheets

Specification includes a Sequence Listing.

(56) References Cited

OTHER PUBLICATIONS

Taylor, Hugh S., et al. "Novel therapies targeting endometriosis." Reproductive sciences 18.9 (2011): 814-823.
Teague et al., "MicroRNA-regulated pathways associated with endometriosis." Mol Endocrinol, 23: 265-275, Dec. 2008, 11 pages.
Teague et al., 2010, The role of microRNAs in endometriosis and associated reproductive conditions. Hum Reprod Update, 16: 142-165.
Ti, Dongdong, et al. "LPS-preconditioned mesenchymal stromal cells modify macrophage polarization for resolution of chronic inflammation via exosome-shuttled let-7b." Journal of translational medicine 13.1 (2015): 1-14.
Turchinovich et al., 2011, "Characterization of extracellular circulating microRNA." Nucleic Acids Res, 39:7223-7233.
Turner, Nicholas C et al. "Advances in the treatment of advanced oestrogen-receptor-positive breast cancer." Lancet (London, England) vol. 389,10087 (2017): 2403-2414. doi:10.1016/S0140-6736(16)32419-9.
U.S. Appl. No. 15/129,663 Examiner Interview Summary dated Nov. 20, 2020, 5 pages.
Ulivi et al., 2014, "miRNAs as non-invasive biomarkers for lung cancer diagnosis." Molecules, 19:8220-8237.
Vercellini, Paolo, et al. "'Waiting for Godot': a commonsense approach to the medical treatment of endometriosis." Human Reproduction 26.1 (2011): 3-13.
Vodolazkaia et al., "Evaluation of a panel of 28 biomarkers for the non-invasive diagnosis of endometriosis." Hum Reprod, 27: 2698-2711, Jun. 26, 2012.
Wang et al., "Correlation and quantitation of microRNA aberrant expression in tissues and sera from patients with breast tumor." Gynecol Oncol, 119: 586-593, Jul. 2010.
Wang et al., 2012, "Circulating MiR-125b as a marker predicting chemoresistance in breast cancer." PLoS One, 7: e34210 (8 pages).
Wang et al., 2012, "Evidence for serum miR-15a and miR-16 levels as biomarkers that distinguish sepsis from systemic inflammatory response syndrome in human subjects." Clin Chem Lab Med, 50:1423-1428.
Wang et al., 2013, "Circulating microRNAs identified in a genome-wide serum microRNA expression analysis as noninvasive biomarkers for endometriosis." J Clin Endocrinol Metab, 98:281-289.
Wang et al., 2015, "MicroRNA-125b may function as an oncogene in lung cancer cells." Mol Med Rep, 11(5):3880-3887.
Wang, et al. Analysis of Serum microRNA Profile by Solexa Sequencing in Women With Endometriosis. Reprod Sci. Oct. 2016;23(10):1359-70. doi: 10.1177/1933719116641761. Epub Jul. 13, 2016.
Wang, Tianzhen, et al. "Aberrant regulation of the LIN28A/LIN28B and let-7 loop in human malignant tumors and its effects on the hallmarks of cancer." Molecular cancer 14.1 (2015): 1-13.
Weber, et al. The microRNA spectrum in 12 body fluids. Clinical chemistry 56.11 (2010): 1733-1741.
Wen-Tao Wang et al, "Circulating MicroRNAs Identified in a Genome-Wide Serum MicroRNA Expression Analysis as Noninvasive Biomarkers for Endometriosis", Journal of Clinical Endocrinology & Metabolism, (Jan. 1, 2013), vol. 98, No. 1, doi:10.1210/jc.2012-2415, ISSN 0021-972X, pp. 281-289, XP055127854.
Wittrup, Anders, and Judy Lieberman. "Knocking down disease: a progress report on siRNA therapeutics." Nature reviews. Genetics vol. 16,9 (2015): 543-52. doi:10.1038/nrg3978.
Wolff, Erin F et al. "Endometrial stem cell transplantation in MPTP-exposed primates: an alternative cell source for treatment of Parkinson's disease." Journal of cellular and molecular medicine vol. 19,1 (2015): 249-56. doi: 10.1111/jcmm.12433.
Xu et al., 2014, "Tumor-suppressing effects of miR451 in human osteosarcoma." Cell Biochem Biophys, 69(1):163-168.
Yang et al., "MicroRNA microarray identifies Let-7i as a novel biomarker and therapeutic target in human epithelial ovarian cancer." Cancer Res, 68: 10307-10314.
Yu, Fengyan, et al. "let-7 regulates self renewal and tumorigenicity of breast cancer cells." Cell 131.6 (2007): 1109-1123.
Zhang, Hong-He et al. "Detection of let-7a microRNA by real-time PCR in gastric carcinoma." World journal of gastroenterology vol. 13,20 (2007): 2883-8. doi:10.3748/wjg.v13.i20.2883.
Zhao et al., 2012, "Circulating microRNA miR-323-3p as a biomarker of ectopic pregnancy." Clin Chem, 58:896-905.
Zhao, Yingchun, et al. "Let-7 family miRNAs regulate estrogen receptor alpha signaling in estrogen receptor positive breast cancer." Breast cancer research and treatment 127.1 (2011): 69-80.
Zhu et al., 2014, Different miRNA expression profiles between human breast cancer tumors and serum. Front Genet, 5:149, 7 pages.
Aartsma-Rus, Annemieke et al. "The importance of genetic diagnosis for Duchenne muscular dystrophy." Journal of medical genetics vol. 53,3 (2016): 145-51. doi:10.1136/jmedgenet-2015-103387.
Afshar, et al. Changes in eutopic endometrial gene expression during the progression of experimental endometriosis in the baboon, Papio anubis.Biology of reproduction 88.2 (2013): 44-1.
Aitana Braza-Bols et al, "MicroRNA expression profile in endometriosis: its relation to angiogenesis and fibrinolytic factors", Human Reproduction, GB, (Mar. 6, 2014), vol. 29, No. 5, doi: 10.1093/humrep/deu019, ISSN 0268-1161, pp. 978-988, XP055402965.
Akao et al., 2007, "MicroRNA-143 and -145 in colon cancer." DNA Cell Biol, 26: 311-320.
Akao, Yukihiro et al. "let-7 microRNA functions as a potential growth suppressor in human colon cancer cells." Biological & pharmaceutical bulletin vol. 29,5 (2006): 903-6. doi:10.1248/bpb.29.903.
Arroyo et al., 2011, "Argonaute2 complexes carry a population of circulating microRNAs independent of vesicles in human plasma." Proc Natl Acad Sci U S A, 108:5003-5008.
Bandiera et al., 2015, "miR-122-a key factor and therapeutic target in liver disease . . . " J Hepatol, 62:448-457.
Bao, Mei-Hua et al. "Let-7 in cardiovascular diseases, heart development and cardiovascular differentiation from stem cells." International journal of molecular sciences vol. 14,11 23086-102. Nov. 21, 2013, doi:10.3390/ijms141123086.
Bartel, David P. "MicroRNAs: target recognition and regulatory functions." cell 136.2 (2009): 215-233.
Bulun, Serdar E et al. "Estrogen production and metabolism in endometriosis." Annals of the New York Academy of Sciences vol. 955 (2002): 75-85; discussion 86-8, 396-406. doi:10.1111/j.1749-6632.2002.tb02767.x.
Chang et al. BMPR1B Up-Regulation via a miRNA Binding Site Variation Defines Endometriosis Susceptibility and CA125 Levels. PLoS One 2013, 8:e80630-e80630, 10 pages.
Chen et al. MiR-125b regulates endometrial receptivity by targeting MMP26 in women undergoing IVF-ET with elevated progesterone on HCG priming day. Scientific reports 6 (2016): 25302. (12 pages).
Chen et al., 2008, "Characterization of microRNAs in serum: a novel class of biomarkers for diagnosis of cancer and other diseases." Cell Res, 18:997-1006.
Chen et al., 2014, "MicroRNA-125b suppresses the proliferation and osteogenic differentiation of human bone marrow-derived mesenchymal stem cells." Mol Med Rep, 9(5):1820-1826.
Cheng, Ching-wen, et al. "Activation of mutated K-ras in donor endometrial epithelium and stroma promotes lesion growth in an intact immunocompetent murine model of endometriosis." The Journal of pathology 224.2 (2011): 261-269.
Cheng, et al. Print CG, Charnock-Jones DS. Activation of mutated K-ras in donor endometrial epithelium and stroma promotes lesion growth in an intact immunocompetent murine model of endometriosis. J Pathol 224.2 (2011): 261-269.
Chin, Lena J et al. "A SNP in a let-7 microRNA complementary site in the KRAS 3' untranslated region increases non-small cell lung cancer risk." Cancer research vol. 68,20 (2008): 8535-40. doi:10.1158/0008-5472.CAN-08-2129.
Cho et al. Aromatase inhibitor regulates let-7 expression and let-7f-induced cell migration in endometrial cells from women with endometriosis. Fertility and sterility 106.3 (2016): 673-680.
Cho et al., "MicroRNAs in Cancer Translational Research", Publication (online). 2011 (retrieved Nov. 11, 2019). DOI 10.1007/978-94-007-0298-1_1, Springer Science+Business Media B.Y. 2011.

(56) References Cited

OTHER PUBLICATIONS

Retrieved from the Internet: <URL: https://dokumen.tips/download/link/micrornas-in-cancer-translational-research->, pp. 1-552, Table 1.1, p. 110, first paragraph.
Cho et al., 2012, "Urinary vitamin D-binding protein is elevated in patients with endometriosis." Hum Reprod, 27:515-522.
Cho et al., 2015, "Circulating microRNAs as potential biomarkers for endometriosis." Fertil Steril, 103(5):1252-1260.
Cho, SiHyun, et al. "Aromatase inhibitor regulates let-7 expression and let-7f-induced cell migration in endometrial cells from women with endometriosis." Fertility and sterility 106.3 (2016): 673-680.
Cho, SiHyun, et al. "Circulating microRNAs as potential biomarkers for endometriosis." Fertility and sterility 103.5 (2015): 1252-1260.
Cho, William CS. MicroRNAs in cancer translational research. Berlin, Germany: Springer, 2011.
Co-pending U.S. Appl. No. 16/860,792, filed Apr. 28, 2020 (82 pages).
Cosar, et al. Serum microRNAs as diagnostic markers of endometriosis: a comprehensive array-based analysis. Fertil Steril. Aug. 2016;106(2):402-9. doi: 10.1016/j.fertnstert.2016.04.013. Epub May 11, 2016.
Coskun et al., 2012, "MicroRNAs in inflammatory bowel disease-pathogenesis, diagnostics and therapeutics . . . " World J Gastroenterol, 18:4629-4634.
D'Hooghe, et al. Lack of an Association between a Polymorphism in the KRAS 3' Untranslated Region (rs61764370) and Endometriosis in a Large European Case-Control Study.Gynecologic and obstetric investigation 84.6 (2019):575-582.
Dall, Genevieve Victoria, and Kara Louise Britt. "Estrogen Effects on the Mammary Gland in Early and Late Life and Breast Cancer Risk." Frontiers in oncology vol. 7 110. May 26, 2017, doi: 10.3389/fonc.2017.00110.
Dorval et al., 2013, "Circulating microRNAs in Alzheimer's disease: the search for novel biomarkers . . . " Front Mol Neurosci, 6:24 (6 pages).
EP15769372.2 Extended Search Report dated Sep. 8, 2017. (11 pages).
EP17847431.8 Extended European Search Report dated Jul. 22, 2020 (15 pages).
EP17847431.8 The Partial Supplemental European Search Report dated Apr. 8, 2020. (14 pages).
EP18852025.8 Extended Search Report dated Aug. 3, 2021.
Figueira, Paula Gabriela Marin et al. "Stem cells in endometrium and their role in the pathogenesis of endometriosis." Annals of the New York Academy of Sciences vol. 1221,1 (2011): 10-7. doi: 10.1111/j.1749-6632.2011.05969.x.
Gallo et al., 2012, "The majority of microRNAs detectable in serum and saliva is concentrated in exosomes." PLoS One, 7: e30679 (5 pages).
Ghazal et al. H19 lncRNA alters stromal cell growth via IGF signaling in the endometrium of women with endometriosis. EMBO molecular medicine 7.8 (2015): 996-1003.
Giray et al., 2014, "Profiles of serum microRNAs; miR-125b-5p and miR223-3p serve as novel biomarkers for HBV-positive hepatocellular carcinoma." Mol Biol Rep, 41(7):4513-4519.
Giudice, Linda C. "Clinical practice: endometriosis." The New England journal of medicine 362.25 (2010): 2389.
Graham et al. The expression of microRNA-451 in human endometriotic lesions is inversely related to that of macrophage migration inhibitory factor (MIF) and regulates MIF expression and modulation of epithelial cell survival. Human Reproduction 30.3 (2015): 642-652.
Grechukhina et al., 2012, "A polymorphism in a let-7 microRNA binding site of KRAS in women with endometriosis." EMBO Mol Med, 4: 206-217.
Harris, Timothy JR, and Frank McCormick. "The molecular pathology of cancer." Nature reviews Clinical oncology 7.5 (2010): 251-265.

Hassan, Mohammad Q., et al. "Non-coding RNAs: epigenetic regulators of bone development and homeostasis." Bone 81 (2015): 746-756.
Hwang, H-W, and J T Mendell. "MicroRNAs in cell proliferation, cell death, and tumorigenesis." British journal of cancer vol. 94,6 (2006): 776-80. doi:10.1038/sj.bjc.6603023.
International Search Report and Written Opinion for App. No. PCT/US19/41532, dated Jan. 6, 2020, 12 pages.
Izawa, Masao et al. "Molecular Background of Estrogen Receptor Gene Expression in Endometriotic Cells." Reproductive sciences (Thousand Oaks, Calif.) vol. 23,7 (2016): 871-6. doi: 10.1177/1933719115623642.
Jancik, Sylwia et al. "Clinical relevance of KRAS in human cancers." Journal of biomedicine & biotechnology vol. 2010 (2010): 150960. doi:10.1155/2010/150960.
Jarry et al., 2014, The validity of circulating microRNAs in oncology: five years of challenges and contradictions. Mol Oncol, 8: 819-829.
Jia et al., 2013, "Plasma miR-17-5p, miR-20a and miR-22 are down-regulated in women with endometriosis." Hum Reprod, 28:322-330.
Jin et al., 2013, "Circulating microRNAs: a novel class of potential biomarkers for diagnosing and prognosing central nervous system diseases . . . " Cell Mol Neurobiol, 5:601-613.
Joshi et al. Altered expression of microRNA-451 in eutopic endometrium of baboons (*Papio anubis*) with endometriosis. Human Reproduction 30.12 (2015): 2881-2891.
Juliano, Rudolph L. "The delivery of therapeutic oligonucleotides." Nucleic acids research vol. 44,14 (2016): 6518-48. doi:10.1093/nar/gkw236.
Karachaliou, Niki et al. "KRAS mutations in lung cancer." Clinical lung cancer vol. 14,3 (2013): 205-14. doi:10.1016/j.cllc.2012.09.007.
Kawada, Kenji, Kosuke Toda, and Yoshiharu Sakai. "Targeting metabolic reprogramming in KRAS-driven cancers." International journal of clinical oncology 22.4 (2017): 651-659.
Kazmi, Hasan Raza, et al. "A let-7 microRNA binding site polymorphism in the KRAS 3' UTR is associated with Increased risk and reduced survival for gallbladder cancer in North Indian population." Journal of cancer research and clinical oncology 142.12 (2016): 2577-2583.
Kranenburg, Marieke, Martin Vlaar, and Berend Smit. "Simulating induced interdigitation in membranes." Biophysical journal 87.3 (2004): 1596-1605.
Lai et al., 2014, "Modulated expression of human peripheral blood microRNAs from infancy to adulthood and its role in aging." Aging Cell, 13:679-689.
Laudanski et al., Expression of selected tumor suppressor and oncogenes in endometrium of women wiht endometriosis, Hum Reprod. Aug. 2009;24(8): 1880-90.
Lee, Banghyun, Hongling Du, and Hugh S. Taylor. "Experimental murine endometriosis induces DNA methylation and altered gene expression in eutopic endometrium." Biology of reproduction 80.1 (2009): 79-85.
Liau, Jau-Yu, et al. "BRAF and KRAS mutations in tubular apocrine adenoma and papillary eccrine adenoma of the skin." Human Pathology 73 (2018): 59-65.
Liu et al., 2014, "MicroRNAs as potential biomarkers for gastric cancer." World J Gastroenterol, 20:12007-12017.
Liu et al., 2016, "MicroRNA-451 inhibits neuroblastoma proliferation, invasion and migration by targeting macrophage migration inhibitory factor." Mol Med Rep, 13(3): 2253-60; doi: 10.3892/mmr.4770.
Luong, et al. No evidence for genetic association with the let-7 microRNA-binding site or other common KRAS variants in risk of endometriosis. Human reproduction 27.12 (2012): 3616-3621.
Markman, Ben et al. "EGFR and KRAS in colorectal cancer." Advances in clinical chemistry vol. 51 (2010): 71-119. doi:10.1016/s0065-2423(10)51004-7.
Marsh et al., "Differential expression of microRNA species in human uterine leiomyoma versus normal myometrium . . . " Fertil Steril, 89: 1771-1776, Dec. 15, 2008.

(56) References Cited

OTHER PUBLICATIONS

Matamala et al., 2015, "Tumor microRNA expression profiling identifies circulating microRNAs for early breast cancer detection." Clin Chem, 61(8):1098-1106.

May et al., 2010, "Peripheral biomarkers of endometriosis: a systematic review." Hum Reprod, 16:651-674.

Mol, et al. "The performance of CA-125 measurement in the detection of endometriosis: a meta-analysis." Fertil Steril, 70: 1101-1108, Dec. 1998.

Moustafa, et al. Accurate diagnosis of endometriosis using serum microRNAs. Am J Obstet Gynecol. Mar. 9, 2020. pii: S0002-9378(20)30321-5. doi: 10.1016/j.ajog.2020.02.050. [Epub ahead of print], 28 pages.

Mu, et al. Expression, regulation and function of MicroRNAs in endometriosis.Die Pharmazie—An International Journal of Pharmaceutical Sciences 71.8 (2016): 434-438.

Murri et al., 2013, "Effects of polycystic ovary syndrome (PCOS), sex hormones, and obesity on circulating miRNA-21, miRNA-27b, miRNA-103, and miRNA-155 expression." J Clin Endocrinol Metab, 98:E1835-1844.

Mutlu, Levent, Demetra Hufnagel, and Hugh S. Taylor. "The endometrium as a source of mesenchymal stem cells for regenerative medicine." Biology of reproduction 92.6 (2015).

Naqvi et al., 2016, "Endometriosis Located Proximal to or Remote From the Uterus Differentially Affects Uterine Gene Expression." Reprod Sci, 23:186-191.

Nematian et al. Systemic inflammation induced by microRNAs: endometriosis-derived alterations in circulating microRNA 125b-5p and Let-7b-5p regulate macrophage cytokine production. The Journal of Clinical Endocrinology & Metabolism 103.1 (2017): 64-74.

Nisenblat, et al. Blood biomarkers for the non-invasive diagnosis of endometriosis. Cochrane Database Syst Rev. May 1, 2016;(5):CD012179. (654 pages).

Notice of Allowability dated Dec. 14, 2021 for U.S. Appl. No. 17/184,894 (pp. 1-2).

Notice of Allowability dated Feb. 1, 2021 for U.S. Appl. No. 16/329,436 (pp. 1-3).

Notice of Allowance dated Jan. 27, 2021 for U.S. Appl. No. 16/329,436 (pp. 1-8).

Notice of Allowance dated Sep. 21, 2021 for U.S. Appl. No. 17/184,894 (pp. 1-7).

Office Action dated Apr. 8, 2020 for U.S. Appl. No. 16/329,436 (pp. 1-19).

Office Action dated Aug. 4, 2021 for U.S. Appl. No. 17/184,894 (pp. 1-6).

Office Action dated Jan. 15, 2020 for U.S. Appl. No. 15/129,663 (pp. 1-12).

Office Action dated Jul. 29, 2019 for U.S. Appl. No. 15/129,663 (pp. 1-11).

Office Action dated Nov. 1, 2018 for U.S. Appl. No. 15/129,663 (pp. 1-12).

Office Action dated Oct. 27, 2020 for U.S. Appl. No. 16/329,436 (pp. 1-20).

Ohlsson et al., 2009, "MicroRNA-regulated pathways associated with endometriosis." Mol Endocrinol, 23:265-275.

Ohlsson Teague, E. Maria C., Cristin G. Print, and M. Louise Hull. "The role of microRNAs in endometriosis and associated reproductive conditions." Human reproduction update 16.2 (2010): 142-165.

Pan et al., "The expression profile of micro-RNA in endometrium and endometriosis and the influence of ovarian steroids on their expression." Mol Hum Reprod, 13: 797-806 (Retracted), Aug. 31, 2007.

PCT/US2015/022986 International Preliminary Report on Patentability dated Sep. 27, 2016. (10 pages).

PCT/US2015/022986 International search report with written opinion dated Aug. 10, 2015, 11 pages.

PCT/US2017/049284 International Search Report and Written Opinion dated Nov. 28, 2017. (15 pages).

PCT/US2018/048649 International Search Report dated Jan. 2, 2019. (14 pages).

Rafaella Petracco et al, "MicroRNA 135 Regulates HOXA10 Expression in Endometriosis", Journal of Clinical Endocrinology & Metabolism, (Dec. 1, 2011), vol. 96, No. 12, doi:10.1210/jc.2011-1231, ISSN 0021-972X, pp. E1925-E1933, XP055187310.

Ramon et al., "microRNAs expression in endometriosis and their relation to angiogenic factors." Hum Reprod, 26:1082-1090, Jan. 17, 2011.

Reis et al., 2012, "Diagnostic value of serum activin A and follistatin levels in women with peritoneal, ovarian and deep Infiltrating endometriosis." Hum Reprod, 27:1445-1450.

Rekker et al., 2013, "Circulating microRNA Profile throughout the menstrual cycle." PLoS One, 8: e81166, (6 pages).

Resnick et al., 2008, "The detection of differentially expressed microRNAs from the serum of ovarian cancer patients using a novel real-time PCR platform." Gynecol Oncol, 112: 55-59.

Ruan Yu et al, "[Study on microRNA expression in endometrium of luteal phase and its relationship with infertility of endometriosis]", Chung-Hua Fu Ch'an K'O Tsa Chih—Chinese Journal of Obstetricsand Gyneco, Chinese Medical Journals Publ. House, CN, (Dec. 1, 2013), vol. 48, No. 12, ISSN 0529-567X, pp. 907-910, XP008170439.

Sayed et al., 2014, "Diagnosis, Prognosis and Therapeutic Role of Circulating miRNAs in Cardiovascular Diseases." Heart Lung Cir, 23:503-510.

Schwarzenbach et al., 2014, "Clinical relevance of circulating cell-free microRNAs in cancer." Nat Rev Clin Oncol, 11:145-156.

* cited by examiner

B

COMPOSITIONS AND METHODS FOR TREATING ENDOMETRIOSIS

CROSS-REFERENCE TO RELATED APPLICATIONS

This application is a U.S. national phase application filed under 35 U.S.C. § 371 claiming benefit to International Patent Application No. PCT/US19/41532, filed Jul. 12, 2019, which is entitled to priority under 35 U.S.C. § 119 (e) to U.S. Provisional Application No. 62/697,457, filed Jul. 13, 2018, each of which applications is hereby incorporated herein by reference in its entirety.

STATEMENT REGARDING FEDERALLY SPONSORED RESEARCH OR DEVELOPMENT

This invention was made with government support under HD052668-01 and HD076422 awarded by the National Institutes of Health. The government has certain rights in the invention.

BACKGROUND OF THE INVENTION

Endometriosis has many symptoms that negatively affect both the reproductive capability and professional/social life of affected women (Culley et al Hum Reprod Update 2013; 19). This disease is characterized by the proliferation and growth of endometrial tissue outside of the uterine cavity that causes pelvic pain, and infertility (Taylor et al., Reprod Sci 2011; 18: 814-23; Giudice, N Engl J Med 2010, 362: 2389-98). The incidence of the endometriosis is approximately 10% in reproductive aged women and 20% to 50% of women with infertility or pelvic pain (Taylor et al., Ann N Y Acad Sci 2002, 955: 89-100). The pathophysiology of endometriosis is not well understood, therefore, current treatment options for endometriosis are limited to manipulation of female sex steroid hormones (Vercellini et al., Hum Reprod 2011, 26: 3-13; Simoens et al., Hum Reprod Update 2007, 13: 395-404). These treatment options have significant side effects and are all contraindicated in women wishing to conceive. Non-hormonal therapies that specifically target the endometriosis are needed.

Micro-RNAs (miRNAs) are small non-coding functional RNA molecules approximately 22 nucleotides in length. They play a critical role in the regulation of gene expression by binding directly to the 3'-untranslated region (3'-UTR) of messenger RNA (mRNA) in a sequence-specific fashion, blocking translation or leading to mRNA degradation (Bartel, Cell 2004, 116: 281-97). miRNAs have a major role in regulation of development and in cellular homeostasis (Hwang et al., Br J Cancer 2006, 94: 776-80; Hassan et al., Bone 2015, 81: 746-56). Additionally, aberrant microRNA expression is linked to many diseases such as cancer (Wang et al., Mol Cancer 2015, 14: 125), cardiovascular disorders (Small et al., Nature 2011, 469: 336-42) and inflammatory diseases (Ti et al., J Transl Med 2015, 13: 308). microRNAs are the potent regulators of gene expression in endometriosis (Teague et al., Hum Reprod Update 2010, 16: 142-65). Distinct miRNA expression profiles have been identified in microarray studies of eutopic and ectopic endometrial tissue samples (Teague et al., Hum Reprod Update 2010, 16: 142-65). It was previously reported that circulating microRNAs, including Let-7b-5p, were significantly decreased in the serum of patients with endometriosis as well as animal models of the disease (Cho et al., Fertil Steril 2015, 103: 1252-60 e1; Seifer et al., Reprod Sci 2017, 24: 376-81). Further, it was reported that decreased Let-7 family members in the endometriosis tissue where they are involved in the regulation of genes such as KRAS and aromatase (Grechukhina et al., EMBO Mol Med 2012, 4: 206-17; Cho et al., Fertil Steril 2016, 106: 673-80).

Development of new method for treating endometriosis are needed. The present invention addresses this unmet need in the art.

SUMMARY OF THE INVENTION

In one aspect, the invention provides a method of treating or preventing endometriosis in a subject in need thereof. In one embodiment, the method comprises administering to the subject an effective amount of an activator of a let-7 microRNA (miRNA). In one embodiment, the let-7 miRNA is selected from the group consisting of let-7a-1, let-7a-2, let-7a-3, let-7b, let-7c, let-7d, let-7e, let-7f-1 let-7f-2, let-7g, and let-7i. In one embodiment, the let-7 miRNA is selected from the group consisting of let-7b-3p and let-7b-5p. In one embodiment, the let-7 miRNA is let-7b-5p.

In one embodiment, the activator is at least one selected form the group consisting of a nucleic acid, peptide, antibody, small molecule, antagonist, aptamer, and peptidomimetic. In one embodiment, the activator is a nucleic acid and the nucleic acid is a miRNA or miRNA mimic. In one embodiment, the miRNA or miRNA mimic is let-7b or let-7b mimic. In one embodiment, the let-7b mimic comprises the sequence UGAGGUAGUAGGUUGUGUGGUU (SEQ ID NO:9).

In one aspect, the invention provides a composition for treating endometriosis. In one embodiment, the composition comprises an activator of a let-7 microRNA (miRNA). In one embodiment, the let-7 miRNA is selected from the group consisting of let-7a-1, let-7a-2, let-7a-3, let-7b, let-7c, let-7d, let-7e, let-7f-1 let-7f-2, let-7g, and let-7i. In one embodiment, the let-7 miRNA is selected from the group consisting of let-7b-3p and let-7b-5p. In one embodiment, the let-7 miRNA is let-7b-5p.

In one embodiment, the activator is at least one selected form the group consisting of a nucleic acid, peptide, antibody, small molecule, antagonist, aptamer, and peptidomimetic. In one embodiment, the activator is a nucleic acid and the nucleic acid is a miRNA or miRNA mimic. In one embodiment, the miRNA or miRNA mimic is let-7b or let-7b mimic. In one embodiment, the let-7b mimic comprises the sequence UGAGGUAGUAGGUUGUGUGGUU (SEQ ID NO:9).

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1, comprising FIG. 1A depicts macroscopic images of lesions from Let-7b treated and untreated groups. FIG. 1B depicts a comparison of total lesion size between the two groups, including fluid filled cystic areas. FIG. 1C depicts the histologic area of actual endometriosis excludes the fluid filled cystic area. The area between the outer and inner green lines was used to calculate the histologic area of lesions. FIG. 1D depicts a comparison of histologic area of lesions; n=5 mice per group. FIG. 1E depicts the difference in mouse endometrial tissue area between Let-7b-treated and control mice (n=5). Data are presented as mean percentage±SEM.; *P=0.03.

FIG. 2, comprising FIG. 2A depicts experimental results demonstrating that Let-7b treatment results in significant decrease in the expression levels of ER-α, ER-β, Cyp19a, KRAS 4A, KRAS 4B, IL-6. relative to the control group. Data are presented as mean percentage —SEM; *, P<0.05. FIG. 2B depicts experimental results demonstrating that the expression of IGF-1, cyclin-D1, MMP-2, TLR-4 and IL-10 were unchanged and that no statistical significance was found. Data are presented as mean percentage±SEM.; *P<0.05.

DETAILED DESCRIPTION

Figure 1A:
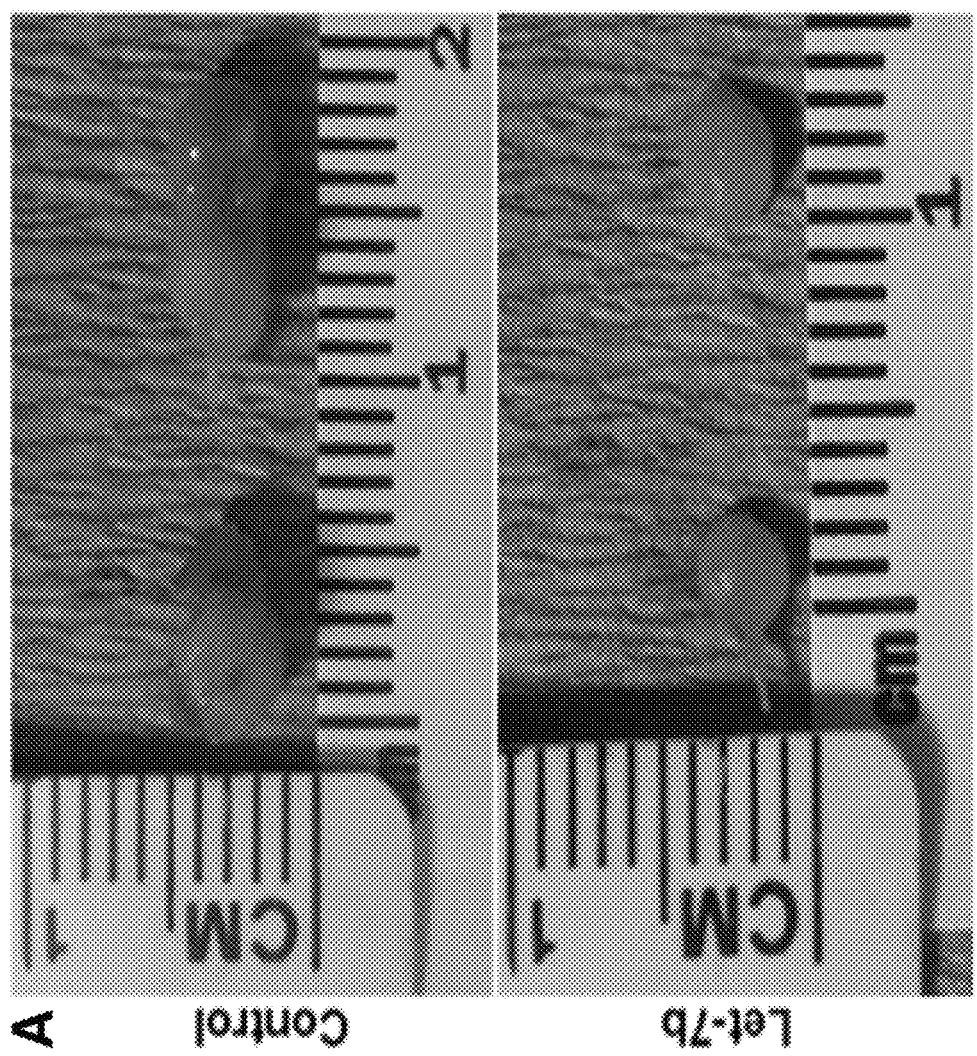
FIG. 1A through FIG. 1E, depicts experimental results demonstrating the macroscopic and microscopic evaluation of lesions.

The present invention relates to compositions and methods for treating and preventing endometriosis. For example, in certain aspects, the present inventions provide compositions for reducing lesion growth.

In one embodiment, the invention relates to modulation of the activity of one or more let-7 miRNAs for the treatment or prevention of endometriosis. For example, in one embodiment, the invention relates to compositions and methods for increasing the expression or activity of one or more let-7 miRNAs. For example, it is described herein that increasing the expression or activity of let-7b results in reduced endometriosis lesion size. It is further demonstrated that let-7b treats endometriosis and simultaneously affects multiple pathways driving endometriosis without systemic hormonal side effects.

In one embodiment, invention relates to compositions and methods for increasing the expression or activity of let-7b-5p or let-7b-3p. For example, in one embodiment, the present invention provides compositions comprising let-7b-5p or let-7b-3p or a let-7b-5p or let-7b-3p mimic. In one embodiment, the present invention provides methods for treating and preventing endometriosis comprising administering let-7b-5p or let-7b-3p or a let-7b-5p or let-7b-3p mimic.

Definitions

Unless defined otherwise, all technical and scientific terms used herein have the same meaning as commonly understood by one of ordinary skill in the art to which this invention belongs. Methods and materials similar or equivalent to those described herein can be used in the practice or testing of the present invention.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "analog" as used herein generally refers to compounds that are generally structurally similar to the compound of which they are an analog, or "parent" compound. Generally, analogs will retain some characteristics of the parent compound, e.g., a biological or pharmacological activity. An analog may lack other, less desirable characteristics, e.g., antigenicity, proteolytic instability, toxicity, and the like. An analog includes compounds in which a particular biological activity of the parent is reduced, while one or more distinct biological activities of the parent are unaffected in the "analog." As applied to polypeptides, the term "analog" may have varying ranges of amino acid sequence identity to the parent compound, for example at least about 70%, at least about 80%-85%, at least about 86%-89%, at least about 90%, at least about 92%, at least about 94%, at least about 96%, at least about 98% or at least about 99% of the amino acids in a given amino acid sequence of the parent or a selected portion or domain of the parent. As applied to polypeptides, the term "analog" generally refers to polypeptides which are comprised of a segment of about at least 3 amino acids that has substantial identity to at least a portion of a binding domain fusion protein. Analogs typically are at least 5 amino acids long, at least 20 amino acids long or longer, at least 50 amino acids long or longer, at least 100 amino acids long or longer, at least 150 amino acids long or longer, at least 200 amino acids long or longer, and more typically at least 250 amino acids long or longer. Some analogs may lack substantial biological activity but may still be employed for various uses, such as for raising antibodies to predetermined epitopes, as an immunological reagent to detect and/or purify reactive antibodies by affinity chromatography, or as a competitive or noncompetitive agonist, antagonist, or partial agonist of a binding domain fusion protein function. As applied to polynucleotides, the term "analog" may have varying ranges of nucleic acid sequence identity to the parent compound, for example at least about 70%, at least about 80%-85%, at least about 86%-89%, at least about 90%, at least about 92%, at least about 94%, at least about 96%, at least about 98% or at least about 99% of the nucleic acids in a given nucleic acid sequence of the parent or a selected portion or domain of the parent. As applied to polynucleotides, the term "analog" generally refers to polynucleotides which are comprised of a segment of about at least 9 nucleic acids that has substantial identity to at least a portion of the parent. Analogs typically are at least 15 nucleic acids long, at least 60 nucleic acids long or longer, at least 150 nucleic acids long or longer, at least 300 nucleic acids long or longer, at least 450 nucleic acids long or longer, at least 600 nucleic acids long or longer, and more typically at least 750 nucleic acids long or longer. Some analogs may lack substantial biological activity but may still be employed for various uses, such as for encoding epitopes for raising antibodies to predetermined epitopes, as a reagent to detect and/or purify sequences by hybridization assays, or as a competitive or noncompetitive agonist, antagonist, or partial agonist of a target or modulator of a target.

"Antisense," as used herein, refers to a nucleic acid sequence which is complementary to a target sequence, such as, by way of example, complementary to a target miRNA sequence, including, but not limited to, a mature target miRNA sequence, or a sub-sequence thereof. Typically, an antisense sequence is fully complementary to the target sequence across the full length of the antisense nucleic acid sequence.

The term "body fluid" or "bodily fluid" as used herein refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "clinical factors" as used herein, refers to any data that a medical practitioner may consider in determining a diagnosis or prognosis of disease. Such factors include, but are not limited to, the patient's medical history, a physical examination of the patient, complete blood count, analysis of the activity of enzymes, examination of cells, cytogenetics, and immunophenotyping of blood cells.

"Complementary" as used herein refers to the broad concept of subunit sequence complementarity between two nucleic acids. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, at least about 60% or at least about 80% of corresponding positions in each of the molecules are occupied by nucleotides which normally base pair with each other (e.g., A:T and G:C nucleotide pairs).

As used herein, "conjugated" refers to covalent attachment of one molecule to a second molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

The term "comparator" describes a material comprising none, or a normal, low, or high level of one of more of the marker (or biomarker) expression products of one or more the markers (or biomarkers) of the invention, such that the comparator may serve as a control or reference standard against which a sample can be compared.

As used herein, the term "derivative" includes a chemical modification of a polypeptide, polynucleotide, or other molecule. In the context of this invention, a "derivative polypeptide," for example, one modified by glycosylation, pegylation, or any similar process, retains binding activity. For example, the term "derivative" of binding domain includes binding domain fusion proteins, variants, or fragments that have been chemically modified, as, for example, by addition of one or more polyethylene glycol molecules, sugars, phosphates, and/or other such molecules, where the molecule or molecules are not naturally attached to wild-type binding domain fusion proteins. A "derivative" of a polypeptide further includes those polypeptides that are "derived" from a reference polypeptide by having, for example, amino acid substitutions, deletions, or insertions relative to a reference polypeptide. Thus, a polypeptide may be "derived" from a wild-type polypeptide or from any other polypeptide. As used herein, a compound, including polypeptides, may also be "derived" from a particular source, for example from a particular organism, tissue type, or from a particular polypeptide, nucleic acid, or other compound that is present in a particular organism or a particular tissue type.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder.

As used herein, the phrase "difference of the level" refers to differences in the quantity of a particular marker, such as a nucleic acid or a protein, in a sample as compared to a control or reference level. For example, the quantity of a particular biomarker may be present at an elevated amount or at a decreased amount in samples of patients with a disease compared to a reference level. In one embodiment, a "difference of a level" may be a difference between the quantity of a particular biomarker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a statistically significant difference between the quantity of a biomarker present in a sample as compared to a control. For example, a difference may be statistically significant if the measured level of the biomarker falls outside of about 1.0 standard deviations, about 1.5 standard deviations, about 2.0 standard deviations, or about 2.5 stand deviations of the mean of any control or reference group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "control or reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

The terms "dysregulated" and "dysregulation" as used herein describes a decreased (down-regulated) or increased (up-regulated) level of expression of a miRNA present and detected in a sample obtained from subject as compared to the level of expression of that miRNA in a comparator sample, such as a comparator sample obtained from one or more normal, not-at-risk subjects, or from the same subject at a different time point. In some instances, the level of miRNA expression is compared with an average value obtained from more than one not-at-risk individuals. In other instances, the level of miRNA expression is compared with a miRNA level assessed in a sample obtained from one normal, not-at-risk subject.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" includes determining the amount of something present, as well as determining whether it is present or absent.

"Differentially increased expression" or "up regulation" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments there between than a comparator.

"Differentially decreased expression" or "down regulation" refers to expression levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments there between than a comparator.

As used herein "endogenous" refers to any material from or produced inside an organism, cell, tissue or system.

The term "expression" as used herein is defined as the transcription and/or translation of a particular nucleotide sequence.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'-ATTGCC-3' and 5'-TATGGC-3' share 50% homology.

As used herein, "homology" is used synonymously with "identity."

"Inhibitors," "activators," and "modulators" of the markers are used to refer to activating, inhibitory, or modulating molecules identified using in vitro and in vivo assays of endometriosis biomarkers. Inhibitors are compounds that, e.g., bind to, partially or totally block activity, decrease, prevent, delay activation, inactivate, desensitize, or down regulate the activity or expression of endometriosis biomarkers. "Activators" are compounds that increase, open, activate, facilitate, enhance activation, sensitize, agonize, or up regulate activity of endometriosis biomarkers, e.g., agonists Inhibitors, activators, or modulators also include genetically modified versions of endometriosis biomarkers, e.g., versions with altered activity, as well as naturally occurring and synthetic ligands, antagonists, agonists, antibodies, peptides, cyclic peptides, nucleic acids, antisense molecules, ribozymes, RNAi, microRNA, and siRNA molecules, small organic molecules and the like. Such assays for inhibitors and activators include, e.g., expressing endometriosis biomarkers in vitro, in cells, or cell extracts, applying putative modulator compounds, and then determining the functional effects on activity, as described elsewhere herein.

As used herein, an "instructional material" includes a publication, a recording, a diagram, or any other medium of expression which can be used to communicate the usefulness of a compound, composition, vector, method or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

As used herein, "microRNA" or "miRNA" describes small non-coding RNA molecules, generally about 15 to about 50 nucleotides in length, in some instances 17-23 nucleotides, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from primary transcripts (pri-miRNA) through sequential cleavage by RNAse III enzymes. miRBase is a comprehensive microRNA database located at www.mirbase.org, incorporated by reference herein in its entirety for all purposes.

A "mutation," as used herein, refers to a change in nucleic acid or polypeptide sequence relative to a reference sequence (which in some instances is a naturally-occurring normal or "wild-type" sequence), and includes translocations, deletions, insertions, and substitutions/point mutations. A "mutant," as used herein, refers to either a nucleic acid or protein comprising a mutation.

"Naturally occurring" as used herein describes a composition that can be found in nature as distinct from being artificially produced. For example, a nucleotide sequence present in an organism, which can be isolated from a source in nature and which has not been intentionally modified by a person, is naturally occurring.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand." Sequences on the DNA strand which are located 5' to a reference point on the DNA are referred to as "upstream sequences." Sequences on the DNA strand which are 3' to a reference point on the DNA are referred to as "downstream sequences."

As used herein, "polynucleotide" includes cDNA, RNA, DNA/RNA hybrid, anti-sense RNA, siRNA, miRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

The term "recombinant DNA" as used herein is defined as DNA produced by joining pieces of DNA from different sources.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "providing a prognosis" refers to providing a prediction of the probable course and outcome of endometriosis, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

"Sample" or "biological sample" as used herein means a biological material isolated from an individual. The biological sample may contain any biological material suitable for detecting the desired biomarkers, and may comprise cellular and/or non-cellular material obtained from the individual.

"Standard control value" as used herein refers to a pre-determined amount of a particular protein or nucleic acid that is detectable in a biological sample. The standard control value is suitable for the use of a method of the present invention, in order for comparing the amount of a protein or nucleic acid of interest that is present in a biological sample. An established sample serving as a standard control provides an average amount of the protein or nucleic acid of interest in the biological sample that is typical for an average, healthy person of reasonably matched background, e.g., gender, age, ethnicity, and medical history. A standard control value may vary depending on the protein or nucleic acid of interest and the nature of the sample (e.g., serum).

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

The terms "treat," "treating," and "treatment," refer to therapeutic or preventative measures described herein. The methods of "treatment" employ administration to a subject, in need of such treatment, a composition of the present invention, for example, a subject afflicted a disease or disorder or a subject who ultimately may acquire such a disease or disorder in order to prevent, cure, delay, reduce the severity of, or ameliorate one or more symptoms of the disorder or recurring disorder, or in order to prolong the survival of a subject beyond that expected in the absence of such treatment.

The terms "underexpress", "underexpression", "underexpressed", or "down-regulated" interchangeably refer to a protein or nucleic acid that is transcribed or translated at a detectably lower level in a biological sample from a woman with endometriosis, in comparison to a biological sample from a woman without endometriosis. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., Q-PCR, RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-, 2-, 3-, 4-, 5-, 6-, 7-, 8-, 9-, 10-fold or more lower levels of transcription or translation in comparison to a control.

The terms "overexpress", "overexpression", "overexpressed", or "up-regulated" interchangeably refer to a protein or nucleic acid (RNA) that is transcribed or translated at a detectably greater level, usually in a biological sample from a woman with endometriosis, in comparison to a biological sample from a woman without endometriosis. The term includes overexpression due to transcription, post transcriptional processing, translation, post-translational processing, cellular localization (e.g., organelle, cytoplasm, nucleus, cell surface), and RNA and protein stability, as compared to a cell from a woman without endometriosis. Overexpression can be detected using conventional techniques for detecting mRNA (i.e., Q-PCR, RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a cell from a woman without endometriosis. In certain instances, overexpression is 1-, 2-, 3-, 4-, 5-, 6-, 7-, 8-, 9-, 10-fold, or more higher levels of transcription or translation in comparison to a cell from a woman without endometriosis.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention relates to compositions and methods for treating endometriosis. For example, in certain aspects, the present inventions provide compositions for reducing lesion growth, and the like. The present invention is based in part upon the discovery that let-7 miRNAs decrease lesion growth and decrease levels of genes that have a role in the pathophysiology of endometriosis, and that the activation of let-7 miRNAs results in the reduction of lesion growth.

In various embodiments of the compositions and methods of the invention described herein, the let-7 miRNA is at least one of let-7 miRNAs. Lethal-7 (let-7) is a founding member of the miRNA family in *C. elegans*. Human orthologs include let-7a, let-7b, let-7c, let-7d, let-7e, let-7f, let-7g, and let-7i. Sequences of let-7 family members are publicly available from miRBase at (www.mirbase.org). Exemplary let-7 miRNAs include, but are not limited to, let-7a (let-7a-1, let-7a-2, let-7a-3), let-7b, let-7c, let-7d, let-7e, let-7f (let-7f-1 and let-7f-2), let-7g, and let-7i. For the following sequences, thymine (T) may be substituted for uracil (U). In one embodiment, let-7a comprises the sequence UUGAUAUGUUGGAUGAUGGAGU (SEQ ID NO: 1). In one embodiment, let-7b comprises the sequence UUGGUGUGUUGGAUGAUGGAGU (SEQ ID NO: 2). In one embodiment, let-7c comprises the sequence UUGGUAUGUUGGAUGAUGGAGU (SEQ ID NO: 3). In one embodiment, let-7d comprises the sequence UGAUACGUUGGAUGAUGGAGA (SEQ ID NO: 4). In one embodiment, let-7e comprises the sequence UAUAUGUUGGAGGAUGGAGU (SEQ ID NO: 5). In one embodiment, let-7f comprises the sequence UUGAUAUGUUAGAUGAUGGAGU (SEQ ID NO: 6). In one embodiment, let-7g comprises the sequence GACAUGUUUGAUGAUGGAGU (SEQ ID NO: 7). In one embodiment, let-7i comprises the sequence

UGUCGUGUUUGUUGAUGGAGU. (SEQ ID NO: 8)

In one aspect, the present invention relates to a composition for treating and preventing endometriosis. In one embodiment, the composition comprises an activator of one or more let-7 miRNAs. For example, in one embodiment, the composition comprises an activator of one or more of let-7a, let-7b, let-7c, let-7d, let-7e, let-7f, let-7g, and let-7i. In one embodiment, the composition comprises an activator of let-7b-3p or let-7b-5p. For example, in one embodiment, the composition comprises a nucleic acid, peptide, antibody, small molecule, antagonist, aptamer, or peptidomimetic that increases the expression or activity of one or more let-7 miRNAs. For example, in certain embodiments, the agent comprises a miRNA or miRNA mimic. In certain embodiments, the agent comprises a let-7 miRNA or a mimic of a let-7 miRNA. For example, in one embodiment, the agent comprises a sequence at least 90% homologous to one or more of SEQ ID NOs:1-8. In one embodiment the agent comprises a sequence at least 90% homologous to

UGAGGUAGUAGGUUGUGUGGUU. (SEQ ID NO: 9)

In one embodiment, the present invention provides a method for treating or preventing endometriosis in a subject. For example, in one embodiment, the method comprises administering to the subject an activator of one or more let-7 miRNAs. For example, in one embodiment, the method comprises administering to the subject an effective amount of an agent that increases the expression or activity of one or more let-7 miRNAs. In one embodiment, the method comprises administering to the subject one or more let-7 miRNAs or let-7 miRNA mimics, including but not limited to the miRNAs of SEQ ID NOs:1-9 or mimics of the miRNAs of SEQ ID NOs:1-9.

Compositions

In one the composition of the present invention comprises an activator of one or more let-7 miRNAs. For example, in one embodiment, the activator of one or more let-7 miRNAs reduces or increases the expression, activity, or both of one or more let-7 miRNAs. In certain embodiments, the activator comprises a nucleic acid, peptide, antibody, small molecule, antagonist, aptamer, or peptidomimetic that increases the expression of one or more let-7 miRNAs, activity of one or more let-7 miRNAs, or a combination thereof.

In one embodiment, the composition comprises an activator of one or more let-7 miRNAs described herein. In one embodiment, the composition comprises an agent that enhances or mimics the expression or activity of one or more let-7 miRNAs. In certain embodiments, the agent comprises a miRNA or miRNA mimic. In certain embodiments, the agent comprises a miRNA of SEQ ID NOs:1-9 or a mimic of a miRNA of SEQ ID NOs:1-9.

In one embodiment, the present invention provides a composition for treating or preventing endometriosis in a subject. In one embodiment, the composition inhibits lesion growth. In certain embodiments, the composition increases the expression, activity, or both of one or more let-7 miRNAs in a cell of the subject.

In one embodiment, the composition of the invention comprises an activator of one or more let-7 miRNAs. An activator of a let-7 miRNA is any compound, molecule, or agent that increases, or activates the function of a let-7 miRNA. For example, an activator of a let-7 miRNA is any compound, molecule, or agent that increases let-7 miRNA expression, activity, or both. In one embodiment, an activator of one or more let-7 miRNAs comprises a nucleic acid, a peptide, a small molecule, a siRNA, a ribozyme, an antisense nucleic acid, an antagonist, an aptamer, a peptidomimetic, or any combination thereof.

It will be understood by one skilled in the art, based upon the disclosure provided herein, that modulating a miRNA encompasses modulating the level or activity of a miRNA including, but not limited to, modulating the transcription, processing, nuclear export, splicing, degradation, binding activity, or combinations thereof. Thus, increasing or activating the level or activity of a miRNA includes, but is not limited to, increasing transcription, processing, nuclear export, splicing, or binding activity, or binding activity or decreasing degradation or combinations thereof and it also includes modulating the level of any nucleic acid or protein that modulates the miRNA level or activity.

Small Molecule

When the activator is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule activator of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the compounds depicted here, as well as the non-salt and non-solvate form of the compounds, as is well understood by the skilled artisan. In some embodiments, the salts of the compounds of the invention are pharmaceutically acceptable salts.

Where tautomeric forms may be present for any of the compounds described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the compounds described. The recitation of the structure or name herein is intended to embrace all possible stereoisomers of compounds depicted. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

In one embodiment, the small molecule compound of the invention comprises an analog or derivative of a compound described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule activators described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog", "analogue," or "derivative" is meant to refer to a chemical compound or molecule made from a parent compound or molecule by one or more chemical reactions. As such, an analog can be a structure having a structure similar to that of the small molecule compounds described herein or can be based on a scaffold of a small molecule compound described herein, but differing from it in respect to certain components or structural makeup, which may have a similar or opposite action metabolically. An analog or derivative of any of a small molecule compound in accordance with the present invention can be used to increase the expression of one or more let-7 miRNAs, the activity of one or more let-7 miRNAs, or both.

In one embodiment, the small molecule compounds described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acids

In certain embodiments, the composition comprises a modulator of one or more let-7 miRNAs described herein. For example, in certain embodiments, the composition comprises an agent that increases the expression or activity of a let-7 miRNA. In one embodiment, the composition comprises an agent that mimics the activity of a let-7 miRNA. In one embodiment, the agent comprises a let-7 miRNA or a mimic of a let-7 miRNA. In one embodiment, the agent comprises a nucleic acid molecule that encodes a let-7 miRNA or mimic of a let-7 miRNA.

In one embodiment, the let-7 miRNA comprises a sequence at least 90% identical to one of SEQ ID NOs:1-9. In one embodiment, the let-7 miRNA comprises a sequence at least 91% identical to one of SEQ ID NOs:1-9. In one embodiment, the let-7 miRNA comprises a sequence at least 92% identical to one of SEQ ID NOs:1-9. In one embodiment, the let-7 miRNA comprises a sequence at least 93% identical to one of SEQ ID NOs:1-9. In one embodiment, the let-7 miRNA comprises a sequence at least 94% identical to one of SEQ ID NOs:1-9. In one embodiment, the let-7 miRNA comprises a sequence at least 95% identical to one of SEQ ID NOs:1-9. In one embodiment, the let-7 miRNA comprises a sequence at least 96% identical to one of SEQ ID NOs:1-9. In one embodiment, the let-7 miRNA comprises a sequence at least 97% identical to one of SEQ ID NOs:1-9. In one embodiment, the let-7 miRNA comprises a sequence at least 98% identical to one of SEQ ID NOs:1-9. In one embodiment, the let-7 miRNA comprises a sequence at least 99% identical to one of SEQ ID NOs:1-9. In one embodiment, the let-7 miRNA comprises a sequence of one of SEQ ID NOs:1-9.

miRNAs are small non-coding RNA molecules that are capable of causing post-transcriptional silencing of specific genes in cells by the inhibition of translation or through degradation of the targeted mRNA. A miRNA can be completely complementary or can have a region of non-complementarity with a target nucleic acid, consequently resulting in a "bulge" at the region of non-complementarity. A miRNA can inhibit gene expression by repressing translation, such as when the miRNA is not completely complementary to the target nucleic acid, or by causing target RNA degradation, which is believed to occur only when the miRNA binds its target with perfect complementarity. The disclosure also can include double-stranded precursors of miRNA. A miRNA or pri-miRNA can be 18-100 nucleotides in length. In one embodiment, the miRNA or pri-miRNA is about 18-80 nucleotides in length. Mature miRNAs can have a length of 19-30 nucleotides. In one embodiment, the mature miRNAs can have a length of about 21-25 nucleotides. In one embodiment, the mature miRNAs can have a length of about 21, 22, 23, 24, or 25 nucleotides. miRNA precursors typically have a length of about 70-100 nucleotides and have a hairpin conformation. miRNAs are generated in vivo from pre-miRNAs by the enzymes Dicer and Drosha, which specifically process long pre-miRNA into functional miRNA. The hairpin or mature microRNAs, or pri-microRNA agents featured in the disclosure can be synthesized in vivo by a cell-based system or in vitro by chemical synthesis.

While, in specific instances, the description may refer to miRNA species having a 5p or 3p notation, the present invention encompasses the use of both the 5p and 3p versions of each miRNA species. Sequences of the miRNA family members are publicly available from miRbase.

In various embodiments, agent comprises an oligonucleotide that contains the nucleotide sequence of a let-7 miRNA. In certain embodiments, the oligonucleotide comprises the nucleotide sequence of a let-7 miRNA in a pre-microRNA, mature or hairpin form. In other embodiments, a combination of oligonucleotides comprising a sequence of one or more let-7 miRNAs, any pre-miRNA, any fragment, or any combination thereof is envisioned.

miRNAs can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism.

Modifications can also increase sequence specificity, and consequently decrease off-site targeting. Methods of synthesis and chemical modifications are described in greater detail below. If desired, miRNA molecules may be modified to stabilize the miRNAs against degradation, to enhance half-life, or to otherwise improve efficacy. Desirable modifications are described, for example, in U.S. Patent Publication Nos. 20070213292, 20060287260, 20060035254, 20060008822, and 2005028824, each of which is hereby incorporated by reference in its entirety. For increased nuclease resistance and/or binding affinity to the target, the single-stranded oligonucleotide agents featured in the disclosure can include 2'-O-methyl, 2'-fluorine, 2'-O-methoxy-ethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleotide modifications can also increase binding affinity to the target. The inclusion of pyranose sugars in the oligonucleotide backbone can also decrease endonucleolytic cleavage. A oligonucleotide can be further modified by including a 3' cationic group, or by inverting the nucleoside at the 3'-terminus with a 3-3' linkage. In another alternative, the 3'-terminus can be blocked with an aminoalkyl group. Other 3' conjugates can inhibit 3'-5' exonucleolytic cleavage. While not being bound by theory, a 3' may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

In one embodiment, the miRNA includes a 2'-modified oligonucleotide containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_{50}$. This modification also increases the nuclease resistance of the modified oligonucleotide. It is understood that the methods and reagents of the present disclosure may be used in conjunction with any technologies that may be developed to enhance the stability or efficacy of an inhibitory nucleic acid molecule.

miRNA molecules include nucleotide oligomers containing modified backbones or non-natural internucleoside linkages. Oligomers having modified backbones include those that retain a phosphorus atom in the backbone and those that do not have a phosphorus atom in the backbone. For the purposes of this disclosure, modified oligonucleotides that do not have a phosphorus atom in their internucleoside backbone are also considered to be nucleotide oligomers. Nucleotide oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriest-ers, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleotide oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyl eneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference. Nucleotide oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleotide oligomer, particularly the 3' position of the sugar on the 3' terminal nucleotide. Nucleotide oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

In other nucleotide oligomers, both the sugar and the internucleoside linkage, i.e., the backbone, are replaced with groups. Methods for making and using these nucleotide oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

In other embodiments, a single stranded modified nucleic acid molecule (e.g., a nucleic acid molecule comprising a phosphorothioate backbone and 2'-OMe sugar modifications is conjugated to cholesterol.

A miRNA described herein, which may be in the mature or hairpin form, may be provided as a naked oligonucleotide that is capable of entering a tumor cell. In some cases, it may be desirable to utilize a formulation that aids in the delivery of a miRNA or other nucleotide oligomer to cells (see, e.g., U.S. Pat. Nos. 5,656,611, 5,753,613, 5,785,992, 6,120,798, 6,221,959, 6,346,613, and 6,353,055, each of which is hereby incorporated by reference).

In some examples, the miRNA composition is at least partially crystalline, uniformly crystalline, and/or anhydrous (e.g., less than 80, 50, 30, 20, or 10% water). In another example, the miRNA composition is in an aqueous phase, e.g., in a solution that includes water. The aqueous phase or the crystalline compositions can be incorporated into a delivery vehicle, e.g., a liposome (particularly for the aqueous phase), or a particle (e.g., a microparticle as can be appropriate for a crystalline composition). Generally, the miRNA composition is formulated in a manner that is compatible with the intended method of administration. A miRNA composition can be formulated in combination with another agent, e.g., another therapeutic agent or an agent that stabilizes an oligonucleotide agent, e.g., a protein that complexes with the oligonucleotide agent. Still other agents include chelators, e.g., EDTA (e.g., to remove divalent cations such as Mg), salts, and RNAse inhibitors (e.g., a broad specificity RNAse inhibitor). In one embodiment, the miRNA composition includes another miRNA, e.g., a second miRNA composition (e.g., a microRNA that is distinct from the first). Still other preparations can include at least three, five, ten, twenty, fifty, or a hundred or more different oligonucleotide species.

In certain embodiments, the composition comprises an oligonucleotide composition that mimics the activity of a let-7 miRNA, described herein. In certain embodiments, the composition comprises oligonucleotides having nucleobase identity to the nucleobase sequence of a let-7 miRNA, and are thus designed to mimic the activity of the let-7 miRNA. In certain embodiments, the oligonucleotide composition that mimics miRNA activity comprises a double-stranded RNA molecule which mimics the mature miRNA hairpins or processed miRNA duplexes In one embodiment, the oligonucleotide shares identity with endogenous miRNA or miRNA precursor nucleobase sequences. An oligonucleotide selected for inclusion in a composition of the present invention may be one of a number of lengths. Such an oligonucleotide can be from 7 to 100 linked nucleosides in length. For example, an oligonucleotide sharing nucleobase identity with a miRNA may be from 7 to 30 linked nucleosides in length. An oligonucleotide sharing identity with a miRNA precursor may be up to 100 linked nucleosides in length. In certain embodiments, an oligonucleotide comprises 7 to 30 linked nucleosides. In certain embodiments, an oligonucleotide comprises 7, 8, 9, 10, 11, 12, 13, 14, 15, 16, 17, 18, 19, 20, 21, 22, 23, 24, 25, 26, 28, 29, or 30 linked nucleotides. In certain embodiments, an oligonucleotide comprises 19 to 23 linked nucleosides. In certain embodiments, an oligonucleotide is from 40 up to 50, 60, 70, 80, 90, or 100 linked nucleosides in length.

In certain embodiments, an oligonucleotide has a sequence that has a certain identity to a miRNA or a precursor thereof. Nucleobase sequences of mature miRNAs and their corresponding stem-loop sequences described herein are the sequences found in miRBase, an online searchable database of miRNA sequences and annotation. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence. The compositions of the present invention encompass oligomeric compound comprising oligonucleotides having a certain identity to any nucleobase sequence version of a miRNAs described herein.

In certain embodiments, an oligonucleotide has a nucleobase sequence at least 60%, 65%, 70%, 75%, 80%, 85%, 90%, 95%, 97%, 98% or 99% identical to the miRNA over a region of 7, 8, 9, 10, 11, 12, 13, 14, 15, 16, 17, 18, 19, 20, 21, 22, 23, 24, 25, 26, 27, 28, 29, or 30 nucleobases. Accordingly, in certain embodiments the nucleobase sequence of an oligonucleotide may have one or more non-identical nucleobases with respect to the miRNA. For example, in one embodiment, the oligonucleotide has a nucleobase sequence at least 60%, 65%, 70%, 75%, 80%, 85%, 90%, 95%, 97%, 98% or 99% identical to the one of SEQ ID NOs:1-9 over a region of 7, 8, 9, 10, 11, 12, 13, 14, 15, 16, 17, 18, 19, 20, 21, 22, 23, 24, 25, 26, 27, 28, 29, or 30 nucleobases.

In certain embodiments, the composition comprises a nucleic acid molecule encoding a miRNA, precursor, mimic, or fragment thereof. For example, the composition may comprise a viral vector, plasmid, cosmid, or other expression vector suitable for expressing the miRNA, precursor, mimic, or fragment thereof in a desired mammalian cell or tissue.

In other related aspects, the invention includes an isolated nucleic acid. In some instances, the activator is an siRNA, antisense molecule, or CRISPR guide RNA, which activates one or more let-7 miRNAs. In one embodiment, the nucleic acid comprises a promoter/regulatory sequence such that the nucleic acid is capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (2008, Current Protocols in Molecular Biology, John Wiley & Sons, New York) and as described elsewhere herein. In one embodiment, siRNA is used to increase the level of one or more let-7 miRNAs. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. In some aspects, the level of one or more let-7 miRNAs can be increased by decreasing the level or activity of a protein or nucleic acid that degrades or inhibits the let-7 miRNAs. Therefore, the present invention also includes methods of increasing levels of one or more let-7 miRNAs using RNAi technology.

In another aspect, the invention includes a vector comprising an siRNA or antisense polynucleotide. In one embodiment, the siRNA or antisense polynucleotide is capable of inhibiting the expression of a target polypeptide. In one embodiment, the siRNA or antisense polynucleotide is capable of increasing the expression of a target miRNA. The incorporation of a desired polynucleotide into a vector and the choice of vectors is well-known in the art as described in, for example, Sambrook et al., supra, and Ausubel et al., supra, and elsewhere herein.

In certain embodiments, the expression vectors described herein encode a short hairpin RNA (shRNA). shRNA are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al., and in Ausubel et al., and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Vectors suitable for the insertion of the polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6N5-His, pVAX1, pZeoSV2, pCI, pSVL and PKSV-10, pBPV-1, pML2d and pTDT1.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al.). In a particular embodiment, the vector is a vector useful for transforming animal cells.

In one embodiment, the recombinant expression vectors may also contain nucleic acid molecules which encode a peptide or peptidomimetic of invention, described elsewhere herein.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue (e.g., skin). Tissue specific promoters are well known in the art and include, but are not limited to, the keratin 14 promoter and the fascin promoter sequences.

In a particular embodiment, the expression of the nucleic acid is externally controlled. In a more particular embodiment, the expression is externally controlled using the doxycycline Tet-On system.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin such as IgG. The selectable markers may be introduced on a separate vector from the nucleic acid of interest.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Recombinant expression vectors may be introduced into host cells to produce a recombinant cell. The cells can be prokaryotic or eukaryotic. The vector of the invention can be used to transform eukaryotic cells such as yeast cells, *Saccharomyces cerevisiae*, or mammal cells for example epithelial kidney 293 cells or U2OS cells, or prokaryotic cells such as bacteria, *Escherichia coli* or *Bacillus subtilis*, for example. Nucleic acid can be introduced into a cell using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987 Tetrahedron Lett. 28:3539-3542; Stec et al., 1985 Tetrahedron Lett. 26:2191-

2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queosine, and wybutosine and the like, as well as acetyl-methyl-, thio- and other modified forms of adenine, cytidine, guanine, thymine, and uridine.

In one embodiment of the invention, an antisense nucleic acid sequence which is expressed by a plasmid vector is used to increase the level of one or more let-7 miRNAs. The antisense expressing vector is used to transfect a mammalian cell or the mammal itself, thereby causing increased endogenous expression one or more let-7 miRNAs.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. In one embodiment, an antisense oligomer comprises between about 10 to about 30 nucleotides. In one embodiment, an antisense oligomer comprises about 15 nucleotides. Antisense oligomers comprising 10-30 nucleotides are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

Compositions and methods for the synthesis and expression of antisense nucleic acids are as described elsewhere herein.

Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). A major advantage of this approach is the fact that ribozymes are sequence-specific.

There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

In one embodiment of the invention, a ribozyme is used to increase the level of one or more let-7 miRNAs. Ribozymes useful for inhibiting the expression of a target molecule which degrades or inhibits a let-7 miRNA may be designed by incorporating target sequences into the basic ribozyme structure which are complementary, for example, to the mRNA sequence encoding a protein which inhibits or degrades one or more let-7 miRNAs. Ribozymes which increase or activate one or more let-7 miRNAs, may be synthesized using commercially available reagents (Applied Biosystems, Inc., Foster City, CA) or they may be genetically expressed from DNA encoding them.

Polypeptides

In other related aspects, the invention includes an isolated peptide that activates one or more let-7 miRNAs. For example, in one embodiment, the peptide of the invention activates one or more let-7 miRNAs directly by binding to, competing with, or acting as a transdominant negative mutant of a protein which inhibits or degrades a let-7 miRNA thereby activating the normal functional activity of the let-7 miRNA.

The variants of the polypeptides according to the present invention may be (i) one in which one or more of the amino acid residues are substituted with a conserved or non-conserved amino acid and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction. The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNALys), could be modified with an amine specific photoaffinity label.

A peptide of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide.

Cyclic derivatives of the peptides or chimeric proteins of the invention are also part of the present invention. Cyclization may allow the peptide or chimeric protein to assume a more favorable conformation for association with other molecules. Cyclization may be achieved using techniques known in the art. For example, disulfide bonds may be formed between two appropriately spaced components having free sulfhydryl groups, or an amide bond may be formed between an amino group of one component and a carboxyl group of another component. Cyclization may also be achieved using an azobenzene-containing amino acid as described by Ulysse, L., et al., J. Am. Chem. Soc. 1995, 117, 8466-8467. The components that form the bonds may be side chains of amino acids, non-amino acid components or a combination of the two. In an embodiment of the invention, cyclic peptides may comprise a beta-turn in the right position. Beta-turns may be introduced into the peptides of the invention by adding the amino acids Pro-Gly at the right position.

In other embodiments, the subject peptide therapeutics are peptidomimetics of the peptides. Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptides.

Moreover, as is apparent from the present disclosure, mimetopes of the subject peptide can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad, Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

Antibodies and peptides may be modified using ordinary molecular biological techniques to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their application. In particular, moieties that improve the stability, biological half-life, water solubility, and immunologic characteristics of the peptide are useful. A non-limiting example of such a moiety is polyethylene glycol (PEG).

Antibodies

The invention also contemplates an antibody, or antibody fragment, specific for a protein which inhibits or degrades a let-7 miRNA thereby activating the normal functional activity of the let-7 miRNA. That is, the antibody can inhibit a protein which inhibits or degrades a let-7 miRNA to treat or prevent endometriosis.

Methods of making and using antibodies are well known in the art. For example, polyclonal antibodies useful in the present invention are generated by immunizing rabbits according to standard immunological techniques well-known in the art (see, e.g., Greenfield et al., 2014, Antibodies, A Laboratory Manual, Cold Spring Harbor, NY). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods.

Monoclonal antibodies directed against full length or peptide fragments of a protein or peptide may be prepared using any well known monoclonal antibody preparation procedures. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art. Further, the antibody of the invention may be "humanized" using methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest.

The invention also includes functional equivalents of the antibodies described herein. Functional equivalents have binding characteristics comparable to those of the antibodies, and include, for example, hybridized and single chain antibodies, as well as fragments thereof.

Functional equivalents include polypeptides with amino acid sequences substantially the same as the amino acid sequence of the variable or hypervariable regions of the antibodies. "Substantially the same" amino acid sequence is defined herein as a sequence with at least 70%, at least about 80%, at least about 90%, at least about 95%, or at least 99% homology to another amino acid sequence (or any integer in between 70 and 99), as determined by the FASTA search method. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')2 fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

Combinations

In one embodiment, the composition of the present invention comprises a combination of modulators described herein. For example, in one embodiment the composition comprises two or more activators of one or more let-7 miRNAs. In certain embodiments, a composition comprising a combination of modulators described herein has an additive effect, wherein the overall effect of the combination is approximately equal to the sum of the effects of each individual modulator. In other embodiments, a composition comprising a combination of modulators described herein has a synergistic effect, wherein the overall effect of the combination is greater than the sum of the effects of each individual modulator. A synergistic effect may be calculated, for example, using suitable methods such as, for example, the Sigmoid-Emax equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

A composition comprising a combination of modulators comprise individual modulators in any suitable ratio. For example, in one embodiment, the composition comprises a 1:1 ratio of two individual modulators. In another embodiment, the composition comprises a 1:1:1 ratio of three individual modulators. However, the combination is not limited to any particular ratio. Rather any ratio that is shown to be effective is encompassed.

Modified Cell

The present invention includes a composition comprising a cell which comprises or expresses a modulator of the invention. In one embodiment, the cell is genetically modified to express a protein and/or nucleic acid of the invention. In certain embodiments, genetically modified cell is autologous to a subject being treated with the composition of the invention. Alternatively, the cells can be allogeneic, syngeneic, or xenogeneic with respect to the subject. In certain embodiment, the cell is able to secrete or release the modulator into extracellular space in order to deliver the modulator to one or more other cells.

The genetically modified cell may be modified in vivo or ex vivo, using techniques standard in the art. Genetic modification of the cell may be carried out using an expression vector or using a naked isolated nucleic acid construct.

In one embodiment, the cell is obtained and modified ex vivo, using an isolated nucleic acid molecule encoding one or more proteins, miRNA, or other nucleic acid molecule described herein. In one embodiment, the cell is obtained from a subject, genetically modified to express the protein and/or nucleic acid, and is re-administered to the subject. In certain embodiments, the cell is expanded ex vivo or in vitro to produce a population of cells, wherein at least a portion of the population is administered to a subject in need.

In one embodiment, the cell is genetically modified to stably express the modulator. In another embodiment, the cell is genetically modified to transiently express the modulator.

Substrates

The present invention provides a scaffold or substrate composition comprising a modulator of the invention, an isolated nucleic acid of the invention, a cell expressing the modulator of the invention, or a combination thereof. For example, in one embodiment, a modulator of the invention, an isolated nucleic acid of the invention, a cell a cell expressing the modulator of the invention, or a combination thereof is incorporated within a scaffold. In another embodiment, a modulator of the invention, an isolated nucleic acid of the invention, a cell expressing the modulator of the invention, or a combination thereof is applied to the surface of a scaffold. The scaffold of the invention may be of any type known in the art. Non-limiting examples of such a scaffold includes a, hydrogel, electrospun scaffold, foam, mesh, sheet, patch, and sponge.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intratumoral, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents, including, for example, chemotherapeutics, immunosuppressants, corticosteroids, analgesics, and the like.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, for example, from about 1 to about 6 nanometers. Such compositions are conveniently in the form of dry powders for administration using a device comprising a dry powder reservoir to which a stream of propellant may be directed to disperse the powder or using a self-propelling solvent/powder dispensing container such as a device comprising the active ingredient dissolved or suspended in a low-boiling propellant in a sealed container. For example, such powders comprise particles wherein at least 98% of the particles by weight have a diameter greater than 0.5 nanometers and at least 95% of the particles by number have a diameter less than 7 nanometers. For example, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (e.g., having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Additionally, the molecules may be delivered using a sustained-release system, such as semipermeable matrices of solid polymers containing the therapeutic agent. Various forms of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Nucleic acids may be included in any of the above-described formulations as the free acids or bases or as pharmaceutically acceptable salts. Pharmaceutically acceptable salts are those salts that substantially retain the biologic activity of the free bases and which are prepared by reaction with inorganic acids. Pharmaceutical salts tend to be more soluble in aqueous and other protic solvents than are the corresponding free base forms.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well-known examples of delivery vehicles that may be used to deliver nucleic acids of the disclosure.

Vaginal Administration

A pharmaceutical composition of the invention may be prepared, packaged, or sold in a formulation suitable for vaginal administration. With respect to the vaginal or perivaginal administration of the compounds of the invention, dosage forms may include vaginal suppositories, creams, ointments, liquid formulations, pessaries, tampons, gels, pastes, foams or sprays. The suppository, solution, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject.

Douche preparations may further comprise various additional ingredients including, but not limited to, antioxidants, antibiotics, antifungal agents, and preservatives.

Treatment Methods

The present invention provides methods of treating or preventing endometriosis or an endometriosis-related disease or disorder. In certain embodiments, the method of the invention comprises administering to a subject an effective amount of a composition that activates or increases the expression, activity, or both of one or more let-7 miRNAs in a cell of the subject. In one embodiment, the method of the invention comprises administering to a subject an effective amount of a composition that mimics the activity of one or more let-7 miRNAs in a cell of the subject. In one embodiment, the method of the invention comprises administering to a subject an effective amount of a composition comprising a let-7 miRNA or a mimic of a let-7 miRNA. In one embodiment, the method of the invention comprises administering to a subject an effective amount of a composition comprising a let-7b miRNA or a mimic of a let-7b miRNA. In one embodiment, the method of the invention comprises administering to a subject an effective amount of a composition comprising a let-7b-5p miRNA or a mimic of a let-7b-5p miRNA. In one embodiment, the method of the invention comprises administering to a subject an effective amount of a composition comprising a let-7b-3p miRNA or a mimic of a let-7b-3p miRNA.

In one aspect, the invention provides a method of reducing lesion growth in a subject in need thereof. In one embodiment, the invention provides a method of reducing lesion size in a subject in need thereof. In one embodiment, the lesion is an endometriosis lesion. In one embodiment, the invention provides a method of decreasing the expression levels of one or more of ER-α, ER-β, Cyp19a, KRAS 4A, KRAS 4B, and IL-6 in a subject in need thereof. In one aspect, the invention provides a method of reducing inflammation. In one embodiments, the method of the invention comprises administering to a subject an effective amount of a composition that activates or increases the expression, activity, or both of one or more let-7 miRNAs in a cell of the subject. In one embodiment, the method of the invention comprises administering to a subject an effective amount of a composition that mimics the activity of one or more let-7 miRNAs in a cell of the subject. In one embodiment, the method of the invention comprises administering to a subject an effective amount of a composition comprising a let-7 miRNA or a mimic of a let-7 miRNA. In one embodiment, the method of the invention comprises administering to a subject an effective amount of a composition comprising a let-7b miRNA or a mimic of a let-7b miRNA. In one embodiment, the method of the invention comprises administering to a subject an effective amount of a composition comprising a let-7b-5p miRNA or a mimic of a let-7b-5p miRNA. In one embodiment, the method of the invention comprises administering to a subject an effective amount of a composition comprising a let-7b-3p miRNA or a mimic of a let-7b-3p miRNA.

Endometriosis related diseases and disorders include, but are not limited to, ovarian cysts, cancer (such as ovarian cancer, breast cancer, non-Hodgkin's lymphoma, and uterine cancer), uterine fibroids, miscarriage and ectopic pregnancy.

Let-7 miRNAs activity can be increased or activated using any method known to the skilled artisan. Examples of methods that increase let-7 miRNA activity, include but are not limited to, increasing the expression of an endogenous gene encoding let-7 miRNA, increasing the expression the let-7 miRNA, and increasing the function, activity, or stability of let-7 miRNA. A let-7 miRNA activator may therefore be a compound that increases expression of a gene encoding let-7 miRNA, increases RNA half-life, stability, or increases let-7 miRNA function, activity or stability. In some aspects, the level of one or more let-7 miRNAs can be increased by decreasing the level or activity of a protein or nucleic acid that degrades or inhibits the let-7 miRNAs. A let-7 miRNA activator may be any type of compound, including but not limited to, a peptide, a nucleic acid, an aptamer, a peptidometic, and a small molecule, or combinations thereof.

Activation of let-7 miRNAs may be accomplished either directly or indirectly. For example, let-7 miRNA may be directly activated by compounds or compositions that directly interact with let-7 miRNA, such as proteins. Levels of let-7 miRNA may be directly increased by administering a let-7 miRNA or a let-7 miRNA mimic. Alternatively, let-7 miRNA may be increased or activated indirectly by compounds or compositions that inhibit regulators which inhibit let-7 miRNA expression.

Modulating expression of an endogenous gene includes providing a specific modulator of gene expression. Decreasing expression of mRNA or protein includes decreasing the half-life or stability of mRNA or decreasing expression of mRNA. Methods of increasing expression or activity of let-7 miRNA include, but are not limited to, methods that use an siRNA, a miRNA, an antisense nucleic acid, CRISPR guide RNA, a ribozyme, an expression vector encoding a transdominant negative mutant, a peptide, a small molecule, and combinations thereof.

Administration of a composition described herein in a method of treatment can be achieved in a number of different ways, using methods known in the art. It will be appreciated that a composition of the invention may be administered to a subject either alone, or in conjunction with another therapeutic agent.

In some embodiments of the methods for treating or preventing endometriosis in a subject in need thereof, a second agent is administered to the subject. For example, in one embodiment, a second endometriosis therapeutic is administered to the subject.

In another embodiment, the invention provides a method to treat endometriosis comprising treating the subject prior to, concurrently with, or subsequently to the treatment with a composition of the invention, with a complementary therapy for the endometriosis, such as surgery, endometriosis therapeutics, including, but not limited to, hormonal therapy, or a combination thereof.

Exemplary endometriosis therapeutics include, but are not limited to, GnRH agonists, including Leuprolide, Goserelin, Nafarelin, Cetrorelix, Ganirelix, and Elagolix; progestins, including medroxyprogesterone acetate, and norethindrone acetate; danazol; combined oral contraceptives; Etonogestrel/ethinyl $E_2$ vaginal ring; levonorgestrel IUD; COX-2 inhibitors, including rofecoxib; PPAR-γ agonists, including Rosiglitazone and Pioglitazone; Aromatase inhibitors including Letrozole and Anastrozole; Selective estrogen receptor modulators including Raloxifene; Statins including simvastatin; immunomodulators, including TNFα inhibitors (e.g. infliximab) or TNF inhibitors (e.g. etancercept); and Valproic acid.

Dosing

In one embodiment, a composition is administered to a subject. The composition may also be a hybrid or fusion to facilitate, for instance, delivery to target cells or efficacy. In one embodiment, a hybrid composition may comprise a tissue-specific targeting sequence. For example, in one embodiment, the composition is targeted to uterine cell.

The therapeutic and prophylactic methods of the invention thus encompass the use of pharmaceutical compositions comprising a modulator described herein, or a combination thereof to practice the methods of the invention. The pharmaceutical compositions useful for practicing the invention may be administered to deliver a dose of from ng/kg/day and 100 mg/kg/day. In one embodiment, the invention envisions administration of a dose which results in a concentration of the compound of the present invention from 1 μM and 10 μM in a mammal.

Typically, dosages which may be administered in a method of the invention to a mammal, for example a human, range in amount from 0.5 μg to about 50 mg per kilogram of body weight of the mammal, while the precise dosage administered will vary depending upon any number of factors, including but not limited to, the type of mammal and type of disease state being treated, the age of the mammal and the route of administration. In one embodiment, the dosage of the compound will vary from about 1 μg to about 10 mg per kilogram of body weight of the mammal. In one embodiment, the dosage will vary from about 3 μg to about 1 mg per kilogram of body weight of the mammal.

The compound may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

In one embodiment, the invention includes a method comprising administering a combination of modulators described herein. In certain embodiments, the method has an additive effect, wherein the overall effect of the administering a combination of modulators is approximately equal to the sum of the effects of administering each individual modulator. In other embodiments, the method has a synergistic effect, wherein the overall effect of administering a combination of modulators is greater than the sum of the effects of administering each individual modulator.

The method comprises administering a combination of modulators in any suitable ratio. For example, in one embodiment, the method comprises administering two individual modulators at a 1:1 ratio. In another embodiment, the method comprises administering three individual modulators at a 1:1:1 ratio. However, the method is not limited to any particular ratio. Rather any ratio that is shown to be effective is encompassed.

One exemplary approach provided by the disclosure involves administration of a recombinant therapeutic, such as a recombinant miRNA molecule, variant, or fragment thereof, either directly to the site of a potential or actual disease-affected tissue or systemically (for example, by any conventional recombinant administration technique). The dosage of the administered miRNA depends on a number of factors, including the size and health of the individual patient. For any particular subject, the specific dosage regimes should be adjusted over time according to the individual need and the professional judgment of the person administering or supervising the administration of the compositions.

A miRNA or miRNA mimic may be administered in dosages between about 1 and 100 mg/kg (e.g., 1, 5, 10, 20, 25, 50, 75, and 100 mg/kg).

Nucleic Acid Based Therapies

The disclosure provides isolated miRNAs and nucleic acid molecules encoding such sequences. A recombinant miRNA or a nucleic acid molecule encoding such a miRNA may be administered to reduce the growth, survival, or proliferation of a tumor or neoplastic cell in a subject in need thereof. In one approach, the miRNA is administered as a naked RNA molecule. In another approach, it is administered in an expression vector suitable for expression in a mammalian cell.

A nucleic acid of the disclosure may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844, 107, 5,877,302, 6,008,336, 6,077,835, 5,972,901, 6,200,801, and 5,972,900, which are incorporated by reference for those aspects.

The nucleic acids may also be administered in combination with a cationic amine such as poly (L-lysine). Nucleic acids may also be conjugated to a chemical moiety, such as transferrin and cholesteryls. In addition, oligonucleotides may be targeted to certain organelles by linking specific chemical groups to the oligonucleotide.

Polynucleotide therapy featuring a nucleic acid molecule encoding a miRNA is another therapeutic approach for treating or preventing endometriosis in a subject. Expression vectors encoding the miRNAs can be delivered to cells of a subject for the treatment or prevention of endometriosis. The nucleic acid molecules must be delivered to the cells of a subject in a form in which they can be taken up and are advantageously expressed so that therapeutically effective levels can be achieved.

Methods for delivery of the nucleic acid molecules to the cell according to the disclosure include using a delivery system, such as liposomes, polymers, microspheres, gene therapy vectors, and naked DNA vectors.

miRNAs may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., BACs and YACs). One of skill in the art would be well equipped to construct a vector through standard recombinant techniques, which are described in Sambrook et al., 2012 and Ausubel et al., 2003, both incorporated herein by reference. Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al, Current Eye Research 15:833-844, 1996; Bloomer et al, Journal of Virology 71:6641-6649, 1997; Naldini et al, Science 272:263-267, 1996; and Miyoshi et al, Proc. Natl. Acad. Sci. U.S.A. 94: 10319, 1997). For example, a nucleotide sequence encoding a miRNA molecule can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244: 1275-1281, 1989; Eglitis et al, BioTechniques 6:608-614, 1988; Tolstoshev et al, Current Opinion in Biotechnology 1:55-61, 1990; Sharp, The Lancet 337: 1277-1278, 1991; Cornetta et al, Nucleic Acid Research and Molecular Biology 36:31 1-322, 1987; Anderson, Science 226:401-409, 1984; Moen, Blood Cells 17:407-416, 1991; Miller et al, Biotechnology 7:980-990, 1989; Le Gal La Salle et al, Science 259:988-990, 1993; and Johnson, Chest 107:77S-83S, 1995). Retroviral vectors are particularly well developed and have been used in clinical settings (Rosenberg et al, N. Engl. J. Med 323:370, 1990; Anderson et al, U.S. Pat. No. 5,399,346).

Other suitable methods for nucleic acid delivery to effect expression of compositions of the present disclosure are believed to include virtually any method by which a nucleic acid (e.g., DNA, including viral and nonviral vectors) can be introduced into an organelle, a cell, a tissue or an organism, as described herein or as would be known to one of ordinary skill in the art.

The administration of a nucleic acid or peptide inhibitor of the invention to the subject may be accomplished using gene therapy. Gene therapy, which is based on inserting a therapeutic gene into a cell by means of an ex vivo or an in vivo technique. Suitable vectors and methods have been described for genetic therapy in vitro or in vivo, and are known as expert on the matter; see, for example, Giordano, Nature Medicine 2 (1996), 534-539; Schaper, Circ. Res 79 (1996), 911-919; Anderson, Science 256 (1992), 808-813; Isner, Lancet 348 (1996), 370-374; Muhlhauser, Circ. Res 77 (1995), 1077-1086; Wang, Nature Medicine 2 (1996), 714-716; WO94/29469; WO97/00957 or Schaper, Current Opinion in Biotechnology 7 (1996), 635-640 and the references quoted therein. The polynucleotide codifying the polypeptide of the invention can be designed for direct insertion or by insertion through liposomes or viral vectors (for example, adenoviral or retroviral vectors) in the cell. In one embodiment, the cell is a cell of the germinal line, an embryonic cell or egg cell or derived from the same. In one embodiment, the cell is a core cell. Suitable gene distribution systems that can be used according to the invention may include liposomes, distribution systems mediated by receptor, naked DNA and viral vectors such as the herpes virus, the retrovirus, the adenovirus and adeno-associated viruses, among others. The distribution of nucleic acids to a specific site in the body for genetic therapy can also be achieved by using a biolistic distribution system, such as that described by Williams (Proc. Natl. Acad. Sci. USA, 88 (1991), 2726-2729). The standard methods for transfecting cells with recombining DNA are well known by an expert on the subject of molecular biology, see, for example, WO94/29469; see also supra. Genetic therapy can be carried out by directly administering the recombining DNA molecule or the vector of the invention to a patient or transfecting the cells with the polynucleotide or the vector of the invention ex vivo and administering the transfected cells to the patient.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. miRNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. For any particular subject, the specific dosage regimes should be adjusted over time according to the individual need and the professional judgment of the person administering or supervising the administration of the compositions.

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Circulating microRNAs as Potential Biomarkers for Endometriosis

Experiments were conducted to examine whether miRNA Let-7b-5p plays a role in the pathogenesis and treatment of endometriosis. The data presented herein demonstrates the therapeutic use of miRNA Let-7b-5p in the treatment of endometriosis in a murine model. Endometriosis was treated using micro-RNA Let-7b or a scrambled control micro RNA. Let-7b treatment resulted in reduced endometriosis lesion size. Decreased gene expression was noted in several genes known to promote endometriosis growth including ER-α, ER-β, Cyp19a, KRAS 4A, KRAS 4B and IL-6. These results indicate that microRNA Let-7b has a pleiotropic role in endometriosis pathophysiology affecting estrogen signaling, inflammation and growth factor receptors. Local treatment of endometriosis with Let-7b is a promising therapy for endometriosis that simultaneously affects multiple pathways driving endometriosis without systemic hormonal side effects.

The materials and methods are now described.

Animals

Six to eight-week old C57BL/6J wild-type female mice were purchased from Jackson Laboratories. Mice were housed 5 animals per cage in a 12-hour light, 12-hour dark cycle (7 AM to 7 PM) with ad libitum access to food and water. Mice were acclimated at least one week and vaginal cytology analysis was performed to determine estrous cycle stage of individual animals prior to surgery. Ten animals that were in diestrus stage were used as recipient and three mice that were in estrus stage were used as donors.

Induction of Endometriosis in Mice

Endometriosis was induced in ten mice using a modified version of the syngeneic endometriosis protocol that has been previously reported (Lee et al., Biol Reprod 2009, 80: 79-85). In accordance with this model, identical sizes of uterine tissue fragments were sutured onto the peritoneal surface. Three mice in estrus stage were euthanized using a $CO_2$ chamber, both uterine horns from each mouse were removed and opened longitudinally and divided into equal fragments measuring 4 $mm^2$. These fragments were preserved on ice in DMEM/F12 Ham 1:1 media until transplantation. For implantation, ten mice were anesthetized by inhalation of isoflurane and laparotomy was performed by midline incision. Two uterine fragments were sutured on each right and left peritoneal surface area using 5-0 polyglactin sutures. Subsequently, the peritoneum and skin were closed with same sutures.

MicroRNA Let-7b-5p Treatment

Ten animals with experimentally induced endometriosis were randomly divided two groups of five mice in each. Two weeks after the induction of endometriosis miRNA Let-7b-5p treatment was initiated with Let-7b-5p mimic (UGAGGUAGUAGGUUGUGUGGUU (SEQ ID NO:9)-mirBase accession number: MIMAT0000522). miRNA cel-miR-67-3p miRNA (UCACAACCUCCUAGAAAGAGUAGA (SEQ ID NO:10)-mirBase accession number: MIMAT0000039) was used as a control. miRNAs were injected into the peritoneal cavity by in vivo-jetPEI carrier (Polyplus-transfection, Illkirch, France). The oligonucleotide+in vivo-jetPEI mixture was prepared according to the manufacturer's guidelines for intraperitoneal oligonucleotide injection. Accordingly, 1.0 ml 5% glucose mixture including 100 μg nucleic acid and 16 μl carrier reagent (N/P=8) was prepared for each injection and mice were treated by intraperitoneal injections for every 3 days for two weeks. The dose chosen was based on previously described in vitro dose response experiments (Cho et al., Fertil Steril 2016, 106: 673-80).

Macroscopic and Microscopic Evaluation of Lesions

After 2 weeks of treatment with Let-7b-5p miRNA, animals were euthanized within a $CO_2$ chamber and endometriotic lesions were removed from peritoneum of the mice. All lesions were individually measured and lesion's volumes were calculated with using smallest $diameter^2 \times$ largest diameter/2 formula. Half of each lesion was kept in RNA stabilization solution for mRNA isolation to determine the gene expression by qRT-PCR analysis and the other half was kept in 4% paraformaldehyde solution for immunohistochemistry studies. After H&E staining all lesions were evaluated under light microscope to confirm endometriosis. The area of each lesion was calculated using the NIS Elements Imaging software program.

RNA Extraction and Quantitative Real-Time Polymerase Chain Reaction

Endometriotic lesions were thawed on ice and minced into fine pieces and homogenized in 1.0 ml of TRIzol reagent, RNA chloroform extracted and precipitated in isopropyl alcohol and dissolved in 30 μl of RNase-free water. The total RNA was purified using the RNeasy cleanup kit, according to the manufacturer's protocol, treated using recombinant shrimp DNase to eliminate DNA contamination and quantified by a NanoDrop spectrophotometer. Purified RNA was immediately used for cDNA synthesis or stored at −80° C. until use later. For cDNA synthesis, purified RNA (1000 ng) was reverse-transcribed using iScript cDNA synthesis kit. Real-time quantitative PCR (real-time qPCR) was performed using SYBR Green and optimized in the MyiQ single-color real-time PCR detection system. Primer sequences used for gene expression are listed in Table 1. The specificity of the amplified transcript and absence of primer-dimers was confirmed by a melting curve analysis. Gene expression was normalized to that of β-actin as an internal control. Relative mRNA expression was calculated using the comparative cycle threshold (Ct) method ($2^{-\Delta CT}$) (Barr, Manning, G Proteins Techniques of Analysis CRC Press, Inc, Boca Raton, FL 1999: 227-45; Livak et al., Methods 2001, 25: 402-8). All experiments were carried out three times and each in duplicate.

TABLE 1

Primer sequences used for gene expression by qRT-PCR

| Gene | | Sequence | SEQ ID NO |
|---|---|---|---|
| ER-α | Forward | TCTGCCAAGGAGACTCGCTACTGT | 11 |
| | Reverse | GCTTGGCCAAAGGTTGGCAG | 12 |
| ER-β | Forward | GCCAACCTCCTGATGCTTCTTT | 13 |
| | Reverse | TTGTACCCTCGAAGCGTGTGA | 14 |
| CYP19A1 | Forward | CTTGGCTGTAGGGGGCATAC | 15 |
| | Reverse | GCGCTATTTGGCCTGAGTTG | 16 |
| KRAS4A | Forward | AGATGTGCCTATGGTCCTGGTAG | 17 |
| | Reverse | CAATCTGTACTGTCGGATCTCTC | 18 |
| KRAS4B | Forward | GATGTGCCTATGGTCCTGGTAG | 19 |
| | Reverse | CATCGTCAACACCCTGTCTTG | 20 |
| IL-6 | Forward | TAGTCCTTCCTACCCCAATTTCC | 21 |
| | Reverse | TTGGTCCTTAGCCACTCCTTC | 22 |

TABLE 1-continued

Primer sequences used for gene expression by qRT-PCR

| Gene | | Sequence | SEQ ID NO |
|---|---|---|---|
| IGF-1 | Forward | GGTGGTTTATGAATGGTT | 23 |
| | Reverse | AGGGTGTGTCTAATGGAG | 24 |
| Cyclin-D1 | Forward | AAGTGCGTGCAGAAGGAGATTGT | 25 |
| | Reverse | GGATAGAGTTGTCAGTGTAGATGC | 26 |
| MMP-2 | Forward | CCCTCAAGAAGATGCAGAAGTTC | 27 |
| | Reverse | TCTTGGCTTCCGCATGGT | 28 |
| TLR-4 | Forward | TTCAGAACTTCAGTGGCTGGATT | 29 |
| | Reverse | CCATGCCTTGTCTTCAATTGTTT | 30 |
| IL-10 | Forward | GCTGCGGACTGCCTTCAG | 31 |
| | Reverse | AGGAGTCGGTTAGCAGTATGTTGTC | 32 |
| β-actin | Forward | AGTGTGACGTTGACATCCGTA | 33 |
| | Reverse | GCCAGAGCAGTAATCTCCTTCT | 34 |

Immunohistochemistry Analysis

Lesions were fixed in 4% paraformaldehyde and embedded in paraffin. Five-micrometer tissue sections were mounted on slides followed by 15 minutes boiling in sodium citrate (pH 6) for antigen retrieval, and blocked with 10% goat serum. Slides were incubated at 4° C. overnight with anti-ER-α (1:300; sc-542; Santa Cruz Biotechnology, Inc.), anti-ER-β (1:500; sc-8974; Santa Cruz Biotechnology, Inc.), anti-aromatase (1:700; ab-18995; Abcam Inc.,), anti-KRAS (1:400; ab-216890; Abcam Inc.) primary antibodies to determine protein expression, respectively. Slides were incubated 60 minutes at room temperature with biotinylated goat anti-rabbit IgG (1:200; Vector Laboratories), and for detection ABC Vectorstain Elite reagents with DAB plus $H_2O_2$ (Vector Laboratories) was used. Tissue sections were counterstained with hematoxylin. Images of stained sections were captured using Nikon eclipse 80i microscope.

Statistical Analysis

GraphPad Prism 7.0 a software was used for all statistical analyses. All in vitro experiments were performed in triplicate and the mean for each individual animal was used for statistical analysis. The quantitative data were tested for normality using the Shapiro-Wilk test. Non-normally distributed continuous variables were compared using Mann-Whitney U test. Student t-test was used for evaluating of normally distributed variables. P<0.05 was considered as statistically significant.

The results are now described.

Let-7b Treatment and Evaluation of Lesions

Figure 1B:
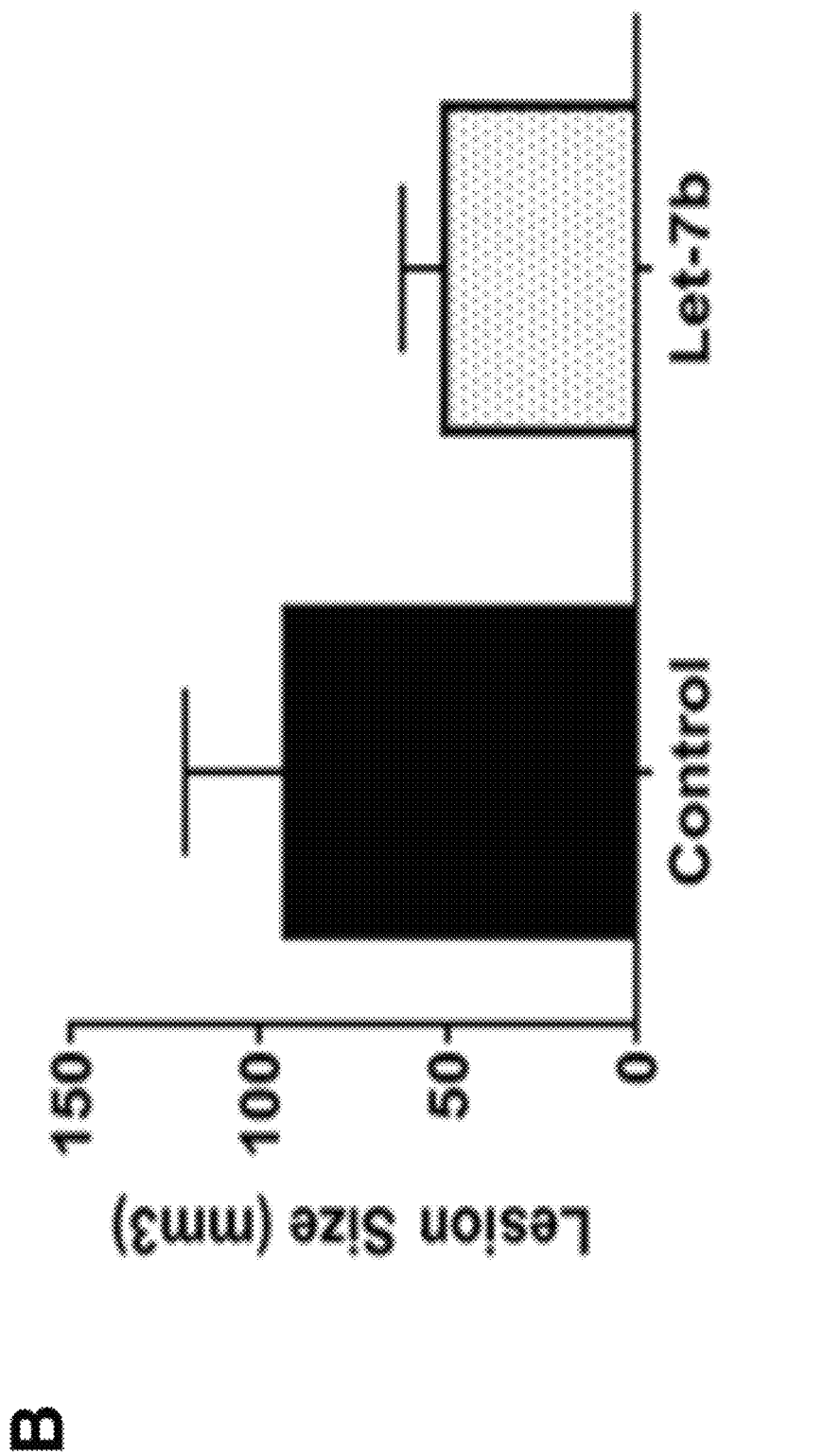
Figure 1C:
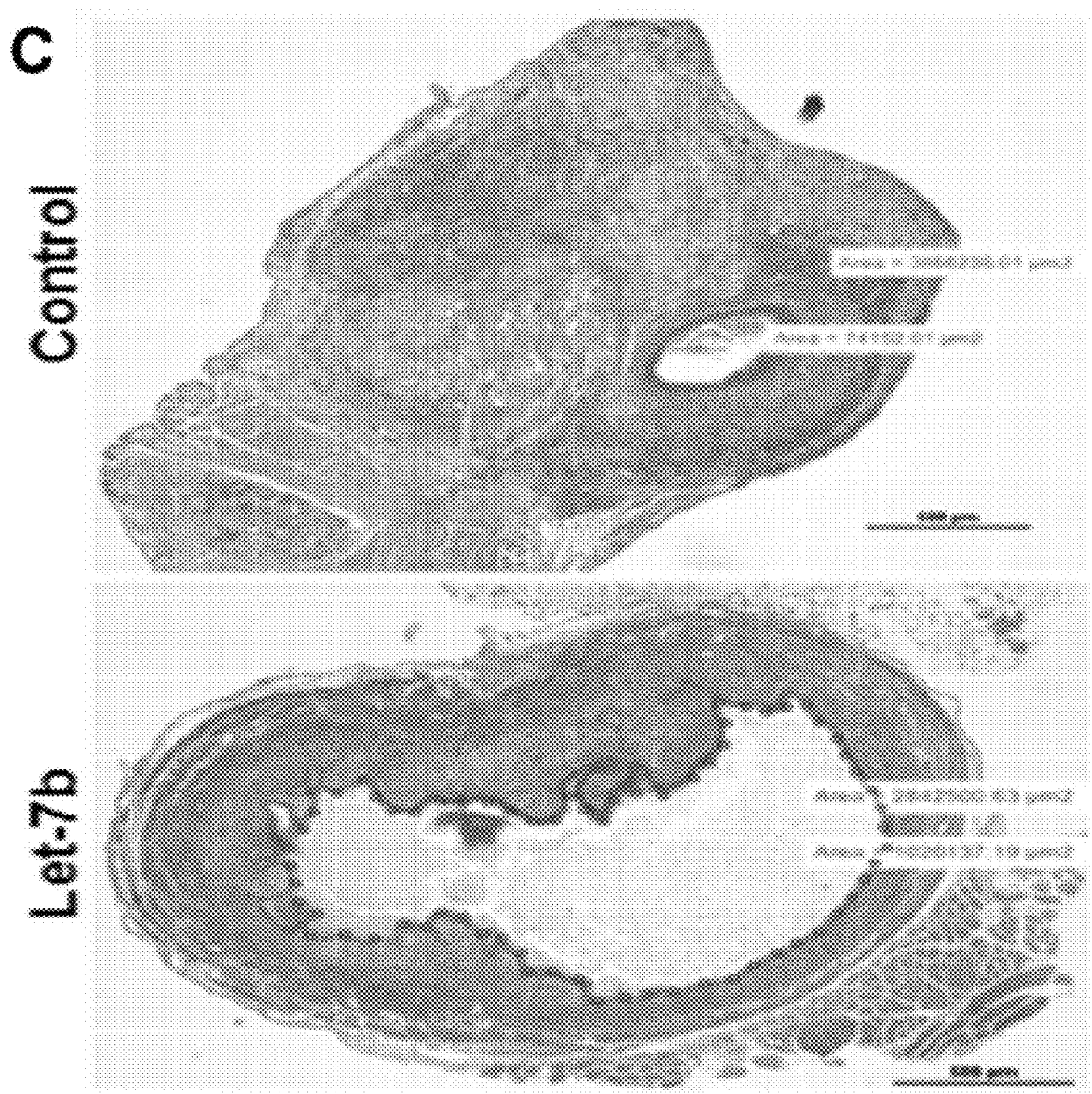
Figure 1D:
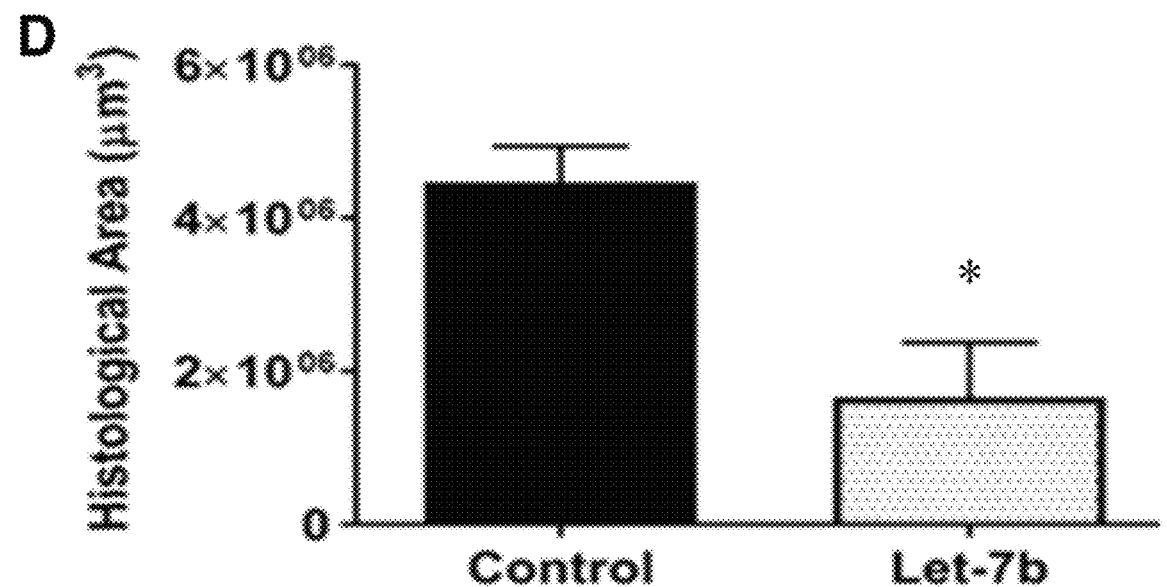
Figure 1E:
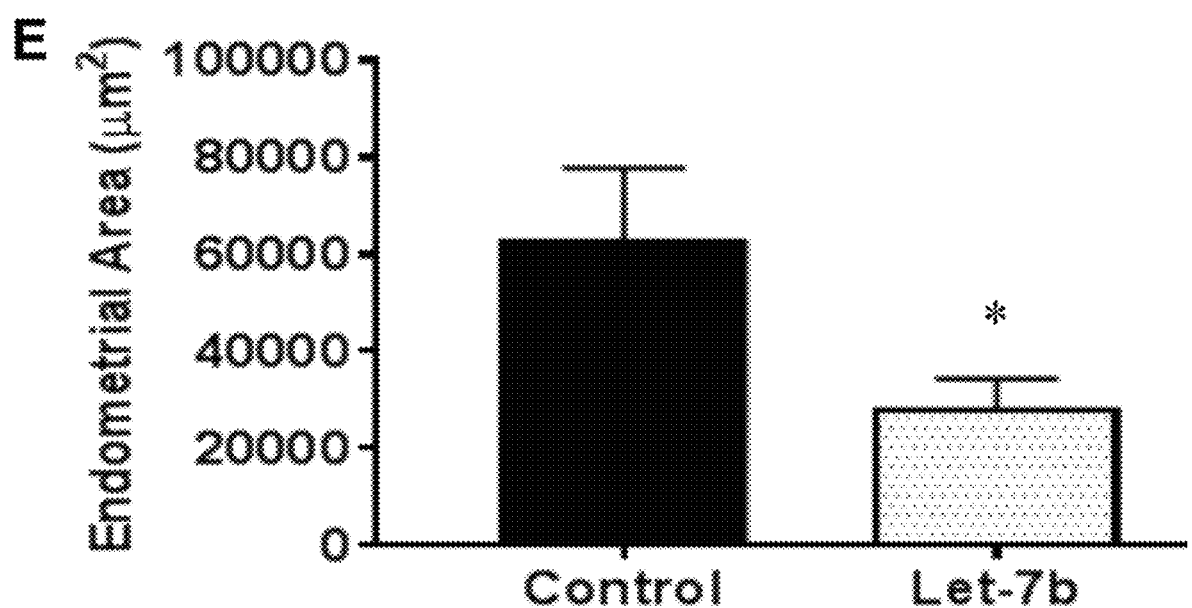

No adverse reactions of the Let-7 treatment were noted. At the end of the miRNA Let-7b-5p treatment period (2-weeks) mice were euthanized and endometriotic lesions collected. First lesion size and volume were compared between the Let-7 treated and control groups. All of the lesions were cystic and the fluid filled portion responded little to this short term treatment. Gross lesion size was lower in the Let-7b treated group, however the difference was not significant (p=0.14) (FIG. 1A and FIG. 1B). Additionally, lesions were compared by measuring histological area of actual endometriosis. The histologic area was evaluated under the microscope to exclude the cystic part of lesions; the fluid filled cystic area was subtracted from the total lesion are to determine the amount of active endometriosis. A significantly diminished histologic endometriosis tissue area was observed in the Let-7b treatment group (p=0.03) (FIG. 1C and FIG. 1D) compared to the control group. The histological area of endometriosis lesions included the grafted myometrium in Let-7b treated and control mice. The area of endometrial tissue was also specifically measured and which was also significantly reduced in Let-7b treated mice compared to control mice, as shown in FIG. 1E.

Differential Expression of Genes that are Involved in Endometriosis

Figure 2A:
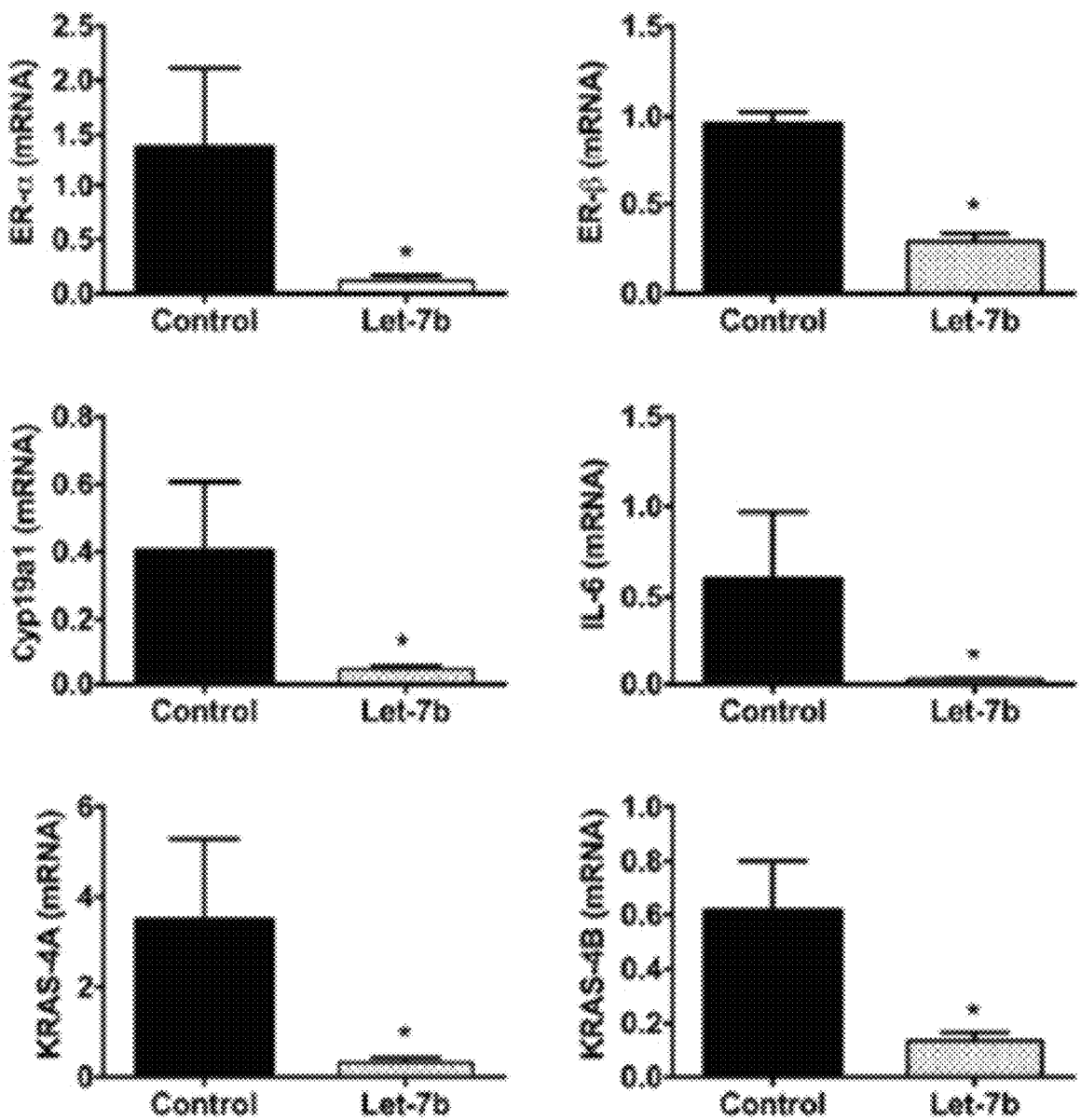
FIG. 2A and FIG. 2B, depicts experimental results demonstrating the effect of Let-7b treatment on mRNA expression of selected genes involved in the pathophysiology of endometriosis as determined by qRT-PCR.
Figure 2B:
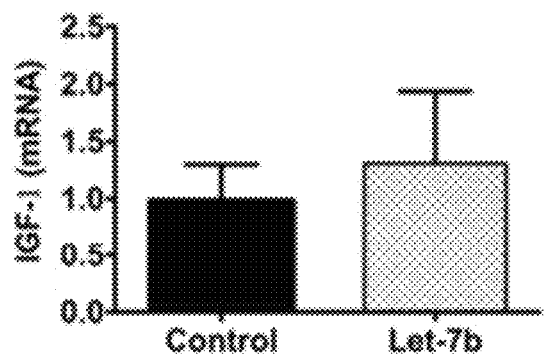
Figure 2B:
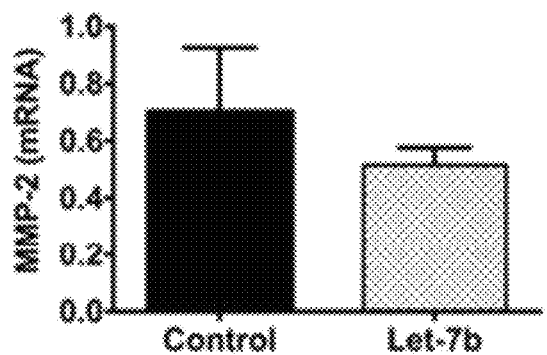
Figure 2B:
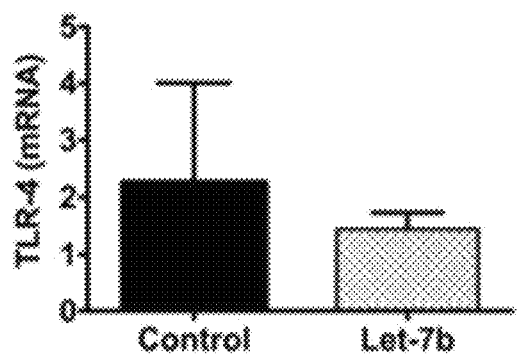
Figure 2B:
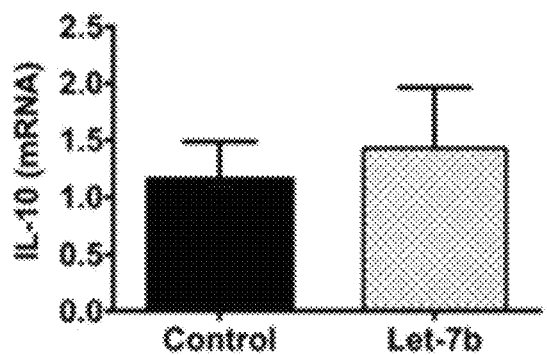
Figure 2B:
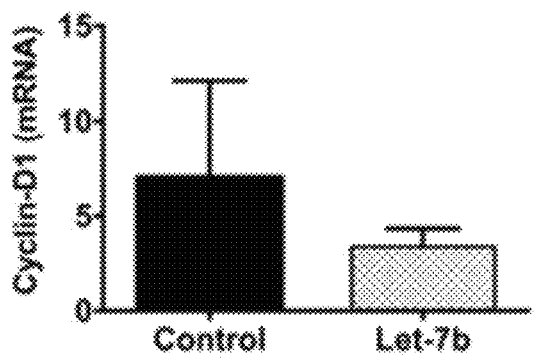

The effect of Let-7b treatment on expression of genes that are involved in endometriosis were determined by qRT-PCR in the lesions and compared with expression in the control group. Decreased expression of several genes known to mediate endometriosis growth or endometriosis-associated inflammation was observed. Expression of ER-α, ER-β, Cyp19a, KRAS 4A, KRAS 4B and IL-6 were all decreased in the Let-7b treatment group compared to control group. The quantitative decrease in gene expression are 11.7 fold (p=0.02) for ER-α, 3.3 fold (p=0.02) for ER-β, 8.9 fold (p=0.02) for Cyp19a, 22.6 fold (p=0.02) for IL-6, 10.9 fold (p=0.02) for KRAS 4A, 4.6 fold (p=0.04) for KRAS 4B in Let-7b treated group compared to untreated group as shown in FIG. 2A. Expression levels of the IGF-1, cyclin-D1, MMP-2, TLR-4 and IL-10 were unchanged between the two groups (p>0.05) as shown in FIG. 2B.

Figure 3:
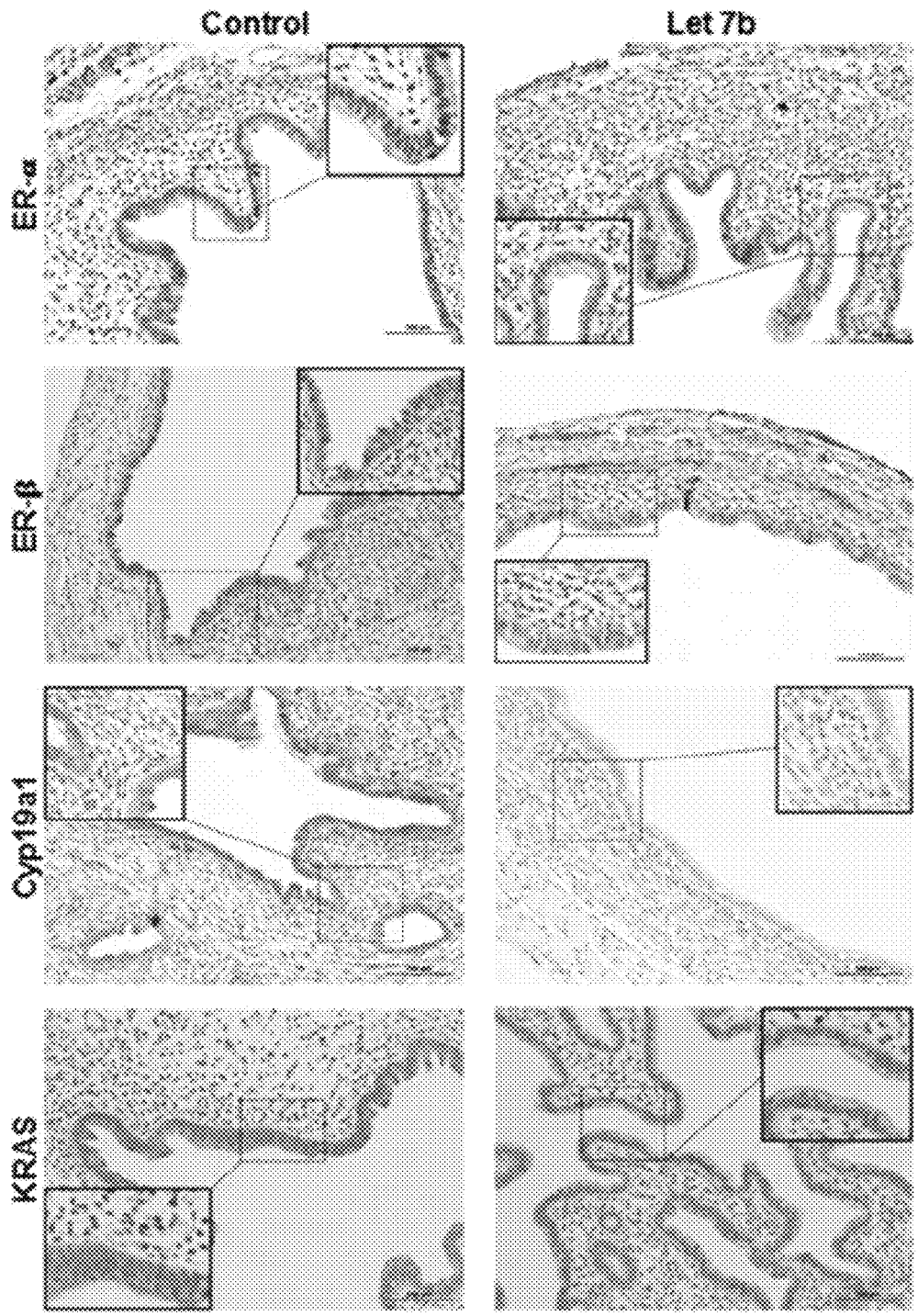
FIG. 3 depicts representative images of protein levels of ER-α, ER-β, Cyp19a and KRAS by immunohistochemical staining. Protein levels were significantly decreased in microRNA Let-7b treated group compared to the control group. Additional panels in each image shows the higher magnification of the immunohistochemical staining that shows the nuclear and/or cytoplasmic localization of the respective protein. (magnification, ×20, Scale bar=100 um).

The differential protein expression level of the genes that were significantly altered in the Let-7b treatment group was confirmed by immunohistochemical analysis. Decreased epithelial and stromal cells nuclear staining and intensity of ER-α staining was observed in the Let-7b treatment group (FIG. 3). Similarly, the intensity of ER-β nuclear staining in epithelial cells was significantly decreased in Let-7b treatment group compared to the untreated group (FIG. 3). Additionally, reduced cytoplasmic expression of Cyp19a1 (and KRAS (FIG. 3) in epithelial cells were determined in Let-7b treatment group compared to the untreated group.

Novel, Non-Hormonal Therapy for Endometriosis

The data presented herein describes a novel, non-hormonal therapy for endometriosis that is based on differential expression of a miRNA in endometriosis. The treatment of endometriosis by intraperitoneal injections of miRNA Let-7b in a murine model appears very promising given that the altered expression of this miRNA is also a key driver of human endometriosis (Takamizawa et al., Cancer Res 2004, 64: 3753-6). Delivery of miRNA Let-7b intraperitoneally in mice showed decreased lesion growth and decreased levels of genes that have a role in the pathophysiology of endometriosis. These results support the hypothesis that miRNAs, especially Let-7b, may be useful as a therapeutic agent/s for the treatment of endometriosis.

Macroscopic evaluation of lesions is one of the tests for determining effectiveness of endometriosis treatment. Therefore, lesions were initially compared using total volume. However, most of the lesions were compromised of fluid filled cystic structures in this rodent endometriosis model. Histologic tissue evaluation proved a more accurate technique than measuring lesion size. While not wishing to be bound to any particular theory, the fluid containing portions of the cystic lesions may also resolve over time as the endometriosis mediated fluid production and inflammation dissipates.

Let-7b has tumor suppressor activity and regulates cell cycle (Wang et al., Mol Cancer 2015, 14: 125). Suppression of Let-7 family members has been reported in many cancers (Takamizawa et al., Cancer Res 2004, 64: 3753-6; Zhang et al., World J Gastroenterol 2007, 13: 2883-8; Akao et al., Biol Pharm Bull 2006, 29: 903-6). KRAS, a potent proto-oncogene (Kazmi et al., J Cancer Res Clin Oncol 2016, 142: 2577-83; Kranenburg, Biochim Biophys Acta 2005, 1756: 81-2) is mutated in a wide variety of human malignancies (Kawada et al., Int J Clin Oncol 2017, 22: 651-9; Karachaliou et al., Clin lung cancer 2013, 14: 205-14; Markman et al., Adv Clin Chem 2010, 51: 71-119; Jancik et al., J Biomed Biotechnol 2010, 2010: 150960; Liau et al., Hum Pathol 2017; Harris et al., Nat Rev Clin Oncol 2010, 7: 251-65) and upregulated in endometriosis. Activation of mutated KRAS in transplanted endometrium triggers endometriosis in mice (Cheng et al., J Pathol 2011, 224: 261-9). Similarly, a polymorphism of a Let-7 binding site in KRAS 3'-UTR causes abnormal KRAS expression as well as increased proliferation and invasion in endometriosis (Grechukhina et al., EMBO Mol Med 2012, 4: 206-17). Let-7b regulates KRAS expression by binding to one or more of 10 Let-7 complementary sites (LCS) in the 3'-UTR of the KRAS gene (Chin et al., Cancer Res 2008, 68: 8535-40). Here, it is shown that both the KRAS 4A and 4B isoforms as well as total KRAS protein expression levels were diminished in the Let-7b treatment group.

Endometriosis is an estrogen dependent disease and estrogen receptors ER-α and β have a role in endometriosis (Izawa et al., Reprod Sci 2016, 23: 871-6). Breast cancer is another estrogen dependent disease where Let-7 also affects ER expression (Dall et al., Front Onco 2017, 7: 110; Turner et al., Lancet 2017, 389: 2403-14). Decreased Let-7 family miRNAs were demonstrated in ER-α positive breast cancers and there was inverse correlation between several Let-7 family members and ER-α expression levels (Zhao et al., Breast Cancer Res Treat 2011, 127: 69-80). Additionally, Let-7 a, b, and i mimics transfected into MCF7 breast cancer cells reduced ER-α transcription activity; the most effective was Let-7b. ER-α is a Let-7 target where Let-7 represses estrogen signaling (Zhao et al., Breast Cancer Res Treat 2011, 127: 69-80). Further, down-regulation of Let-7 miRNAs has been reported in breast tumor-initiating cells (BT-IC), and restoration of Let-7 in these cells caused reduced proliferation and mammosphere formation in vitro as well as tumor formation, and metastasis in NOD/SCID mice (Yu et al., Cell 2007, 131: 1109-23). We, previously identified stem cells in endometrium and endometriosis (Figueira et al., Ann N Y Acad Sci 2011, 1221: 10-7; Mutlu et al., Biol Reprod 2015, 92: 138; Wolff et al., J Cell Mol Med 2015, 19: 249-56). While not being bound by theory, Let-7 may also regulates stem cells in endometriosis in a similar manor to regulation of BT-IC in breast cancers. In the model, ER-α expression was more strongly suppressed than ER-β with Let-7b miRNA suggesting that Let-7 blocks estrogen stimulation in the treatment of endometriosis. These data suggests a targeted means of blocking sex steroid action in endometriosis without the systemic side effects of whole body estrogen deprivation.

Aromatase P450 has an essential role in estrogen synthesis and has been demonstrated to regulate local estrogen production in endometriosis (Bulun et al., Ann N Y Acad Sci 2002, 955: 75-85, discussion 6-8, 396-406). It was previously shown that high Let-7f expression was significantly correlated with low aromatase protein levels in primary breast cancer stromal cells (Shibahara et al., J Pathol 2012, 227: 357-66). A Let-7f binding site was also identified in Cyp19a1, indicating that the aromatase gene is a direct target of Let-7f (Shibahara et al., J Pathol 2012, 227: 357-66). Similar results were shown in endometrial stromal cells from endometriosis patients and in ishikawa cells (Cho et al., Fertil Steril 2016, 106: 673-80). Significantly increased Let-7b and Let-7f expression levels were determined after aromatase inhibitor treatment. Further, decreased aromatase expression and reduced endometrial cell migration was shown after Let-7f mimic transfection (Cho et al., Fertil Steril 2016, 106: 673-80). High levels of Let-7b after aromatase inhibitor treatment indicated that Let-7b has a role in aromatase regulation and decreased aromatase levels after Let-7b treatment supported that Let-7b treatment reduces local estrogen production and action.

Endometriosis is also a chronic inflammatory disease and macrophages have a principal role in this inflammatory process. An increase in M1 type macrophages is seen in endometriosis (Takebayashi et. al., Am J Reprod Immunol 2015, 73: 221-31). Let-7b may regulate inflammation through its known target gene TLR-4, which regulates M1 macrophage response (Bao et. al., Int J Mol Sci 2013, 14: 23086-102). A trend toward decreased levels of TLR-4 was observed in the Let-7b treatment group compared to controls. Another inflammatory marker, IL-6 levels were significantly suppressed in the Let-7b treatment group. These results suggest that Let-7b treatment does reduce inflammation associated with endometriosis.

In this study a local treatment route was used for miRNA Let-7b treatment. The effective delivery of the oligonucleotides to target cells after systemic administration is not very effective as they are eliminated from the blood stream by hepatic degradation. Therefore, many of the systemic oligonucleotide treatment studies have focused on liver disease (Wittrup et al., Nat Rev Genet 2015, 16: 543-52). Various types of oligonucleotide carriers have been used to resolve these problems, however none of them has fully accomplished targeted oligonucleotide delivery (Juliano, Nucleic Acids Res 2016, 44: 6518-48). The most effective oligonucleotide based drugs approved by the U.S. Food and Drug Administration (FDA) are designed for intravitreal injection where local delivery is very effective (Aartsma-Rus, Mol Ther 2016, 24: 193-4). While not wishing to be bound to any particular theory, this drug may work well as an intraperitoneal therapy delivered at the time of surgery or by injection. Further, dose response and safety studies will be required prior to human application.

In conclusion, microRNA Let-7b treatment of endometriosis resulted in decreased estrogen signaling (ER and Cyp19A1), decreased KRAS and decreased inflammatory signaling (IL-6). The pleiotropic effects of Let-7b treatment suggest that multiple complimentary mechanisms were responsible for the actions of Let-7b in endometriosis. These numerous effects suggest the potential for a more comprehensive endometriosis therapy without the systemic effects, a common feature of current drugs.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating endometriosis in a subject with endometriosis, comprising administering to the subject an effective amount of an activator of a let-7 microRNA (miRNA), wherein the activator is a let-7b mimic comprising the sequence UGAGGUAGUAGGUUGUGUGGUU (SEQ ID NO:9), and wherein the activator is administered to the subject by intraperitoneal injections every three days for two weeks.

* * * * *

SEQUENCE LISTING

<160> NUMBER OF SEQ ID NOS: 34

<210> SEQ ID NO 1
<211> LENGTH: 22
<212> TYPE: RNA
<213> ORGANISM: Artificial Sequence
<220> FEATURE:
<223> OTHER INFORMATION: let-7a

<400> SEQUENCE: 1
uugauauguu ggaugaugga gu                                            22

<210> SEQ ID NO 2
<211> LENGTH: 22
<212> TYPE: RNA
<213> ORGANISM: Artificial Sequence
<220> FEATURE:
<223> OTHER INFORMATION: let-7b

<400> SEQUENCE: 2
uuggugyguu ggaugaugga gu                                            22

<210> SEQ ID NO 3
<211> LENGTH: 22
<212> TYPE: RNA
<213> ORGANISM: Artificial Sequence
<220> FEATURE:
<223> OTHER INFORMATION: let-7c

<400> SEQUENCE: 3
uugguauguu ggaugaugga gu                                            22

<210> SEQ ID NO 4
<211> LENGTH: 21
<212> TYPE: RNA
<213> ORGANISM: Artificial Sequence
<220> FEATURE:
<223> OTHER INFORMATION: let-7d

<400> SEQUENCE: 4
ugauacguug gaugauggag a                                             21

<210> SEQ ID NO 5
<211> LENGTH: 20
<212> TYPE: RNA
<213> ORGANISM: Artificial Sequence
<220> FEATURE:
<223> OTHER INFORMATION: let-7e

<400> SEQUENCE: 5
uauauguugg aggauggagu                                               20

<210> SEQ ID NO 6
<211> LENGTH: 22
<212> TYPE: RNA
<213> ORGANISM: Artificial Sequence
<220> FEATURE:
<223> OTHER INFORMATION: let-7f

<400> SEQUENCE: 6
uugauauguu agaugaugga gu                                            22

<210> SEQ ID NO 7
<211> LENGTH: 20
<212> TYPE: RNA
<213> ORGANISM: Artificial Sequence

```
<220> FEATURE:
<223> OTHER INFORMATION: let-7g

<400> SEQUENCE: 7
gacauguuug augauggagu                                                    20

<210> SEQ ID NO 8
<211> LENGTH: 21
<212> TYPE: RNA
<213> ORGANISM: Artificial Sequence
<220> FEATURE:
<223> OTHER INFORMATION: let-7i

<400> SEQUENCE: 8
ugucguguuu guugauggag u                                                  21

<210> SEQ ID NO 9
<211> LENGTH: 22
<212> TYPE: RNA
<213> ORGANISM: Artificial Sequence
<220> FEATURE:
<223> OTHER INFORMATION: let-7b mimic

<400> SEQUENCE: 9
ugagguagua gguugugugg uu                                                 22

<210> SEQ ID NO 10
<211> LENGTH: 24
<212> TYPE: RNA
<213> ORGANISM: Artificial Sequence
<220> FEATURE:
<223> OTHER INFORMATION: cel-miR-67-3p

<400> SEQUENCE: 10
ucacaaccuc cuagaaagag uaga                                               24

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
tctgccaagg agactcgcta ctgt                                               24

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gcttggccaa aggttggcag                                                    20

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
gccaaccucc tgatgcttct tt                                                 22
```

```
<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
ttgtaccctc gaagcgtgtg a                                              21

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cttggctgta gggggcatac                                                20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gcgctatttg gcctgagttg                                                20

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
agatgtgcct atggtcctgg tag                                            23

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
caatctgtac tgtcggatct ctctc                                          25

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
gatgtgccta tggtcctggt ag                                             22

<210> SEQ ID NO 20
<211> LENGTH: 21
<212> TYPE: DNA
<213> ORGANISM: Artificial Sequence
<220> FEATURE:
<223> OTHER INFORMATION: primer
```

```
<400> SEQUENCE: 20
catcgtcaac accctgtctt g                                          21

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
tagtccttcc taccccaatt tcc                                        23

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
ttggtcctta gccactcctt c                                          21

<210> SEQ ID NO 23
<211> LENGTH: 18
<212> TYPE: DNA
<213> ORGANISM: Artificial Sequence
<220> FEATURE:
<223> OTHER INFORMATION: primer

<400> SEQUENCE: 23
ggtggtttat gaatggtt                                              18

<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24
agggtgtgtc taatggag                                              18

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
aagtgcgtgc agaaggagat tgt                                        23

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
ggatagagtt gtcagtgtag atgc                                       24

<210> SEQ ID NO 27
```

```
<211> LENGTH: 23
<212> TYPE: DNA
<213> ORGANISM: Artificial Sequence
<220> FEATURE:
<223> OTHER INFORMATION: primer

<400> SEQUENCE: 27
ccctcaagaa gatgcagaag ttc                                              23

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
tcttggcttc cgcatggt                                                    18

<210> SEQ ID NO 29
<211> LENGTH: 23
<212> TYPE: DNA
<213> ORGANISM: Artificial Sequence
<220> FEATURE:
<223> OTHER INFORMATION: primer

<400> SEQUENCE: 29
ttcagaactt cagtggctgg att                                              23

<210> SEQ ID NO 30
<211> LENGTH: 23
<212> TYPE: DNA
<213> ORGANISM: Artificial Sequence
<220> FEATURE:
<223> OTHER INFORMATION: primer

<400> SEQUENCE: 30
ccatgccttg tcttcaattg ttt                                              23

<210> SEQ ID NO 31
<211> LENGTH: 18
<212> TYPE: DNA
<213> ORGANISM: Artificial Sequence
<220> FEATURE:
<223> OTHER INFORMATION: primer

<400> SEQUENCE: 31
gctgcggact gccttcag                                                    18

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
aggagtcggt tagcagtatg ttgtc                                            25

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
```

```
agtgtgacgt tgacatccgt a                                              21

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
gccagagcag taatctcctt ct                                             22
```